US012256674B2

(12) United States Patent
Schloesser

(10) Patent No.: US 12,256,674 B2
(45) Date of Patent: Mar. 25, 2025

(54) DETASSELER AND CONTROL SYSTEM AND METHOD

(71) Applicant: Oxbo International Corporation, Byron, NY (US)

(72) Inventor: Christopher M. Schloesser, Byron, NY (US)

(73) Assignee: Oxbo International Corporation, Byron, NY (US)

( * ) Notice: Subject to any disclaimer, the term of this patent is extended or adjusted under 35 U.S.C. 154(b) by 0 days.

(21) Appl. No.: 17/205,920

(22) Filed: Mar. 18, 2021

(65) Prior Publication Data

US 2021/0289707 A1   Sep. 23, 2021

Related U.S. Application Data

(60) Provisional application No. 62/992,025, filed on Mar. 19, 2020.

(51) Int. Cl.
*A01D 47/00* (2006.01)
*A01D 34/00* (2006.01)
(Continued)

(52) U.S. Cl.
CPC .............. *A01D 47/00* (2013.01); *B60K 35/00* (2013.01); *A01B 79/005* (2013.01);
(Continued)

(58) Field of Classification Search
CPC .... A01D 47/00; A01D 41/141; A01D 45/021; A01D 34/008; A01D 34/54; A01D 91/02;
(Continued)

(56) References Cited

U.S. PATENT DOCUMENTS

| 2,419,991 A | 5/1947 | Dunning |
| 3,724,184 A | 4/1973 | Wright |

(Continued)

FOREIGN PATENT DOCUMENTS

| CN | 202819218 | 3/2013 |
| CN | 103004579 | 4/2013 |
| CN | 106857227 | 6/2017 |

OTHER PUBLICATIONS

EP Search Report related to corresponding EP 21163770 dated Aug. 6, 2021, seven pages.

(Continued)

*Primary Examiner* — Douglas M Wilson
(74) *Attorney, Agent, or Firm* — Merchant & Gould P.C.

(57) ABSTRACT

A detasseling apparatus includes a chassis having a head mounted to the chassis. The head supports a plurality of row units, each of the row units having an independently adjustable vertical position. Each row unit is independently vertically adjustable. Each row unit includes a puller or cutter, a height adjustment assembly for independently adjusting vertical position of the detasseling assembly to maintain the puller or cutter at a predetermined height relative to seed corn plants being engaged, and an optical sensing assembly. The optical sensing assembly includes a first photoelectric sensor at a first sensor height and a second photoelectric sensor at a second sensor height, the first sensor height being above the second sensor height. A processor receives and stores detasseling data related to detasseling including corn height, depth of cut, height after cutting. The information may be shown on displays to the operator, stored on board the detasseler and/or transmitted to a central control center.

24 Claims, 24 Drawing Sheets

(51) Int. Cl.
| | |
|---|---|
| *A01D 34/54* | (2006.01) |
| *A01D 41/14* | (2006.01) |
| *A01D 45/00* | (2018.01) |
| *A01D 45/02* | (2006.01) |
| *A01D 91/02* | (2006.01) |
| *A01H 1/02* | (2006.01) |
| *B60K 35/00* | (2024.01) |
| *B60K 35/22* | (2024.01) |
| *G01B 11/04* | (2006.01) |
| *A01B 79/00* | (2006.01) |
| *B60K 35/28* | (2024.01) |

(52) U.S. Cl.
CPC ............ *A01D 34/008* (2013.01); *A01D 34/54* (2013.01); *A01D 41/141* (2013.01); *A01D 45/00* (2013.01); *A01D 45/021* (2013.01); *A01D 91/02* (2013.01); *A01H 1/02* (2013.01); *B60K 35/22* (2024.01); *B60K 35/28* (2024.01); *G01B 11/043* (2013.01)

(58) Field of Classification Search
CPC .. A01D 45/00; B60K 35/00; B60K 2370/152; B60K 35/22; B60K 35/28; A01H 1/02; A01B 79/005; G01B 11/043
See application file for complete search history.

(56) References Cited

U.S. PATENT DOCUMENTS

| | | | |
|---|---|---|---|
| 4,041,681 A | | 8/1977 | Chapa |
| 4,219,991 A | * | 9/1980 | Bray ..................... A01D 47/00 171/58 |
| 4,250,697 A | * | 2/1981 | Bray ..................... A01D 47/00 171/58 |
| 4,319,445 A | | 3/1982 | Coats |
| 4,890,447 A | * | 1/1990 | Grandinetti ............ A01D 47/00 56/63 |
| 5,014,503 A | * | 5/1991 | Morin .................... A01D 47/00 56/63 |
| 6,962,210 B1 | | 11/2005 | Redenius |
| 7,647,753 B2 | | 1/2010 | Schlipf |
| 9,609,806 B2 | | 4/2017 | Schlipf et al. |
| 10,244,680 B2 | | 4/2019 | Schlipf et al. |
| 10,342,176 B2 | | 7/2019 | Hashimoto |
| 2012/0304610 A1 | | 12/2012 | Dunn |
| 2012/0304620 A1 | | 12/2012 | Dunn |
| 2013/0118066 A1 | | 5/2013 | Cope |
| 2014/0083073 A1 | | 3/2014 | Doerscher, Sr. |
| 2017/0303470 A1 | * | 10/2017 | Briquet-Kerestedjian ................... A01D 41/141 |
| 2018/0014463 A1 | * | 1/2018 | Hashimoto ............ A01D 47/00 |
| 2018/0199502 A1 | * | 7/2018 | Briquet-Kerestedjian ................... A01D 47/00 |
| 2021/0000010 A1 | * | 1/2021 | Gunda ................... A01D 47/00 |
| 2021/0137006 A1 | * | 5/2021 | Shearer ................ A01D 75/182 |

OTHER PUBLICATIONS

Use of corn height measured with an acoustic sensor improves yield estimation with ground based active optical sensors, L.K. SHarma et al., Computers and Electronics in Agriculture 124 (2016) 254-262.

UAV Based Remote Sensing for Tassel Detection and Growth Stage Estimation of Maize Crop using F-RCNN, A. Kumar et al., Department of Electrical Engineering, Indian Institute of Technology, Hyderabad, India (2019), 3 pages.

\* cited by examiner

FIG. 20

*Crop data calibration*

MAX Boom Raised SAVE
MIN Boom Lowered SAVE 984 mm
Toolbar Height Adj

| | | |
|---|---|---|
| UNCUT CROP H | 0.0FT | 0 |
| UNCUT CROP H | 0.0FT | 0 |
| UNCUT CROP H | 2.2FT | 2 |
| H OF CUT/PULL | 18.0IN | 1 |
| CUT CROP HEI | 3.7FT | 3 |
| CUT CROP HEI | 3.7FT | 3 |
| CUT CROP HEI | 1.8FT | 1 |
| | 5 | |

| | | | | | | |
|---|---|---|---|---|---|---|
| MAX UNCUT CROP HEIGHT | 0.0FT | 0.0FT | 0.0FT | 0.0FT | 0.0FT | 0.0FT |
| MIN UNCUT CROP HEIGHT | 0.0FT | 0.0FT | 0.0FT | 0.0FT | 0.0FT | 0.0FT |
| AVG UNCUT CROP HEIGHT | 2.2FT | 2.2FT | 2.2FT | 2.2FT | 2.2FT | 2.2FT |
| DEPTH OF CUT/PULL | 18.0IN | 18.0IN | 18.0IN | 18.0IN | 18.0IN | 18.0IN |
| MAX CUT CROP HEIGHT | 3.7FT | 3.7FT | 3.7FT | 3.7FT | 3.7FT | 3.7FT |
| MIN CUT CROP HEIGHT | 3.7FT | 3.7FT | 3.7FT | 3.7FT | 3.7FT | 3.7FT |
| AVG CUT CROP HEIGHT | 1.8FT | 1.8FT | 1.8FT | 1.8FT | 1.8FT | 1.8FT |
| | 1 | 2 | 3 | 4 | 5 | 6 |

172

DETASSELER AND CONTROL SYSTEM AND METHOD

BACKGROUND OF THE INVENTION

Field of the Invention

The present invention relates to a system and method for automatically mechanically detasseling seed corn and managing data acquired during detasseling related to the seed corn and the detasseling operations.

Description of the Prior Art

Corn plants have both a male and female flower. The tassel at the very top of corn plants is the male flower that produces the pollen and the ear of the corn with the silk is the female flower. Wind blows pollen from the tassel that falls on the silk. Each strand of silk connects to a different individual ovule on the ear of corn. The pollen pollinates the ovule that develops into a seed. It can be appreciated that corn will typically pollinate itself without human intervention.

However, it is desirable to produce hybrid corn with improved characteristics. By cross-pollinating pollen from one variety of corn with the tassels of another, a hybrid corn may be achieved with improved characteristics. It can be appreciated that this cross-pollination with one variety of corn pollinating the silk of another produces hybrid corn that may obtain hybrids with superior characteristics such as higher yield, improved resistance to drought and/or disease, and other advantageous characteristics. It should be appreciated that corn plants do not pass these characteristics to their offspring and each generation must be newly bred.

To cross-pollinate different varieties, the tassels of the select corn plants are removed to leave the female flower. Therefore, pollen from a different variety must be used to cross-pollinate the female plants. While the tassel is still rolled up in top leaves of the corn plant, the corn is detasseled in which the tassel is removed from the plant. This process of removing selected tassels has traditionally been performed manually and the tassel pulled by hand. In some methods, the tops of plants are mechanically cut off to improve access to the tassels and therefore to improve pulling. The tassels are pulled a few days after cutting the tops of the seed corn plants. In addition, tassels are left on other corn plants, "male" plants, to provide cross-pollination to those in which the tassels have been removed. To control such detasseling, fields are typically planted in a particular pattern so that the plants that are detasseled may be tracked. For example, a field may be planted in a pattern with one row of male plants and then four rows of female plants, followed by another row of male plants and then four rows of female plants in a repeating pattern. Seeds from cross-pollinated corn may then be harvested as a hybrid seed and used for producing corn. To achieve a hybrid seed having sufficient purity, a high percentage of the tassels from the "female" plants must be removed. It can also be appreciated that the window for removing the tassels is very short, very labor intensive and therefore expensive.

Mechanical detasselers have been developed that are able to remove the tassels from the seed corn plants. However, to maintain the purity of the hybrid seed, a high removal percentage of tassels must be maintained. It can be appreciated that corn plants in a field will vary in height. Therefore, maintaining the proper height of detasseling machinery is essential and provides a challenge to attain the quick response needed for controlling mechanized detasseling equipment. As different areas of fields may have plants that have grown more or less, such detasseling equipment must be able to quickly change the height of the detasselers so that the entire tassel is removed. Moreover, it can be appreciated that if too much of the plant is removed during cutting, yield may be affected. Therefore, it is critical that an optimal amount of the top of the corn plant is removed during detasseling. Minimizing leaf loss while removing the entire tassel is critical for maximizing crop yield. Agricultural systems have been developed that use radar and sonar systems. However, such radar and sonar systems may provide false adjustments for detasseling as such systems are unable to detect and measure the top of individual corn plants.

It can therefore be seen that a new and improved automated mechanical detasseling system is needed. Such a system should provide for mechanically removing the tassels from corn plants and automatically adjusting height as the detasseling equipment moves through a field. Such a system should be based on directly sensing the top of the tassels rather than the distance from the ground. Such a system should provide for acquiring data in real time on the seed corn as the equipment moves through the field and for reporting such data for managing equipment and agricultural practices for the seed corn. Moreover, such systems should be responsive, precise and accurate to optimize pulling and/or cutting so that only the proper amount of the top of the corn plants are removed. The present invention addresses these as well as other problems associated with automated corn detasseling.

SUMMARY OF THE INVENTION

The present invention is directed to a system and method for automatically mechanically detasseling seed corn.

A detasseler system includes a chassis supporting a detasseling head. The head includes a toolbar supporting row units that include pullers or cutters. The toolbar is mounted on a supporting linkage to adjust the height of the toolbar supporting the row units. Depending on the number of row units supported and the width of the toolbar, the toolbar may have multiple sections including a center section and folding outer sections (wings) for travel and storage. The chassis is typically supported on four wheels and includes a cab and a motor. It can be appreciated that the chassis may be configured for use in applications other than detasseling such as supporting sprayers or other agricultural implements. The detasseling head is therefore interchangeable with other types of heads performing other agricultural tasks. It can be appreciated that the wheels maintain the chassis high off the ground so that it may drive over tall plants such as corn and cause minimal damage to the field.

The detasseling head includes both the toolbar support linkage and the toolbar. The toolbar support linkage provides for adjusting the height of the entire toolbar. As explained hereinafter, in a first embodiment, row units include two cutters and are individually adjustable for more precise and more efficient detasseling. A single linkage assembly mounts the toolbar to the chassis. The linkage includes a frame assembly attached to the chassis. A pair of upper links and lower links are pivotally mounted to the frame as well as to the head. Hydraulic cylinders extend and retract to raise and lower the linkage. Cross members provide added support and stability. By extending and retracting the hydraulic cylinders, the upper links and lower links pivot upward and downward and therefore adjust the overall height of the toolbar.

The toolbar includes sections extending laterally to the left and the right and support row units with each row unit supporting two pullers or cutters. The pullers and cutters are grouped in pairs so that row unit includes two individual pullers or cutters. There is a space between the center row units and the outer row units to accommodate the male corn plants, which are left alone with the tassels in place.

In one embodiment, each row unit include two cutters with each of the cutters supported on a cross member. The height of the row units is adjustable so that both cutters move up and down together. The row unit framework supports and arranges hydraulic lines, a cutter bracket and a height adjustment assembly.

Each of the cutters includes a support bracket. The support bracket supports a hydraulic motor that drives rotary cutting blades. The hydraulic motor is connected to one of the hydraulic lines. The blades rotate throughout a slightly downward angled plane to engage the tops of the corn plants and remove the optimal amount without imparting further damage to the corn plants. A shield protects the motor and prevents the plants from catching on the bracket. The bracket forms somewhat of a peak to divert corn stalks to one side or the other to the path of the blades. A rear rubber flap provides for a smooth disengagement from the cutter assemblies after passing over the corn plants. The individual plants are directed toward the cutters by guides that extend forward and include portions funneling the plants toward the center of the shield and the blades.

A height adjustment assembly mounts to the framework and extends forward. The height adjustment assembly includes a linear actuator. A linkage includes the linear actuator, an upper link and a lower link. The linkage supports a sensor support bracket, which in turn supports opposed optical sensor assemblies.

The optical sensor assemblies includes laterally opposed sensor pairs so that they pass on either side of two rows of corn that are engaged by the cutters. The opposed sensor assemblies include an upper sensor and a lower sensor on each assembly. The opposed optical sensor sender/receiver pairs therefore can detect whether the optical path between the pair of upper optical sensors is blocked or unblocked and whether the optical path between the opposed lower is blocked or unblocked. The upper optical sensors and the lower optical sensors are therefore able to determine where the top of the corn plants between the sensors is. It can be appreciated that to maintain the tops of the corn plants at a height between the upper sensors and lower sensors, the height adjustment assembly is adjusted so that the optical path between the lower pair of optical sensors is blocked, but the optical path between the upper pair of optical sensors is open. To maintain proper cutting height, the row unit is lowered if the optical path between the lower optical sensors is not blocked. The height of the row unit is raised if the optical path between the opposed upper optical sensors is blocked. In a first condition, the beams of both the upper and lower pair of sensors are received. In such a condition, the row unit is too high and will be lowered until the lower beam is not received. In this second condition, the row unit is at the proper height. In a third condition, both the upper and lower beams are not received, indicating the row unit it too low and will be raised until the upper beam is received. It can be appreciated that the linear actuator is extended and retracted to move the height adjustment assembly.

The row unit framework mounts to the toolbar for individual adjustment of the pairs of cutter assemblies. The framework includes a telescopically slidable inner portion and an outer portion. It can be appreciated that the present invention provides for adjusting the overall height of the toolbar by lowering or raising the toolbar support linkage. The present invention provides for further individual adjustment of each of the row units assemblies and the two associated cutters, or pullers, as explained below. It can therefore be appreciated that variations in the plants may be generally adjusted for by the operator in the cab to raise or lower the toolbar by actuating the linkage and more precise control and height adjustment is made through the sensor assemblies automatically maintaining the cutters at the proper height.

In a further embodiment, the row unit includes pullers rather than cutters. The pullers and cutters and may be interchangeably mounted and removed with quick release mechanisms. Hydraulic connections through the hydraulic lines simply need to be changed. The puller row units mount to the toolbar and attach to the hydraulic lines and include guides in a manner similar to that for the pullers. The height adjustment components are also maintained. For the pullers, each assembly includes a support bracket supporting a pair of counter rotating opposed wheels (tires). At least one of the tires is driven by a hydraulic motor and a rotating shaft. Slightly different guides direct the tassels to the point of engagement between each pair of opposed tires. A curved discharge chute extends over the rear exit of the counter rotating tires. The curved discharge chute is mounted at an angle and curves along an axis substantially parallel to the rotational axis of the tires. The discharge chute therefore directs portions of tassels removed downward and rearward. In operation, the pullers advance along the rows of corn with the plants being directed between the guides to the center of the opposed counter rotating tires. The tires pinch the tassel and is pulled from the remainder of the corn plant. Proper height is again maintained with the height adjustment optical sensors and linkage operating in the same manner as described above. It can be appreciated that the mechanized pulling of tassels substantially reduces the labor previously required for manual detasseling. Moreover, it has been found that the percentage of tassels removed is sufficiently high to meet the standards for cross-pollination of fields of seed companies to achieve hybrid seed having acceptable purity.

It can be appreciated that for some applications, a tassel pulling operation is performed. Cutting may be performed prior to pulling operation to cut the top of the seed corn plant including the tassels to improve the pulling. The combination of cutting and pulling ensures that a sufficiently high percentage of tassels of the "female" plants are removed to conduct cross-pollination. The pulling operations previously have generally been conducted manually. However, according to the present invention, pulling and/or cutting may be performed mechanically with a single detasseling system.

The present invention also automatically acquires data on the detasseling operations and the corn. Such data may be used for other operations. With the dimensions and positions of the various components of the toolbar, the row units, the cutters and the pullers precisely and accurately known, many of the characteristics of the corn and the operations performed can be determined. With use of GPS and other systems, the precise location of the seed corn and its characteristics are known. The chassis dimension, the tool bar support linkage dimensions and angles, the row unit dimensions and the dimensions and angles of the linear actuators are known and/or determined with sensors. Therefore, optical sensor pairs sensing the top of the corn plants and the relative positon of the optical sensor pairs provide for determining the height of the corn. Moreover, as the distance between the optical sensor pairs and the cutters is known the height of the corn after cutting is also known. The present invention is able to determine the height from the ground to the top of the plant, the depth of the cut made, the height of the remaining crop after cutting, as well as the height of the plant at the time of pulling. Such information may be utilized for mapping the fields and may be utilized to identify problem areas and/or sections that may require further follow up operations. Such information also provides data that may be used for estimating yield and timing for future operations. Moreover, with narrow windows for cutting and pulling, where detasselers are used by many seed corn growers and need to cover multiple fields, the data may be used for fleet management of equipment to improve its utilization.

In addition to acquiring various information, the present invention also includes an interactive display screen in the cab for the operator to monitor the detasseling operations and to make adjustments as necessary. The various optical sensors and the adjustment linkages each include position sensors to determine the height of the various assemblies. The present invention may also include wireless technology such as a modem for providing real time information and downloading to a central database. An interactive display screen may provide for adjusting the optical sensors to ensure that the sensors are at their proper vertical position relative to the pullers or cutters. The data also provides information that may require raising or lowering the toolbar in unison. Various performance parameters of the detasseler can also be monitored. The present invention enables calibrating the sensors to ensure that only an appropriate amount of tassel is being properly engaged for pulling or that the top of the plant is being cut at the proper height. The screen may display all row unit heights and show a comparison among each of the row units. Such display provides real time easily understood graphics that allow the operator to perceive the relative uncut crop height, the cut crop height, and the depth of the cut. Information related to minimum and maximum crop heights before and after cutting and the overall depth of the cut or pull for each of the cutting or puller assemblies may be provided. The information provides for making the adjustments prior to entering each field and to also making real-time on the fly adjustments as may be necessary, depending on the crop and operating conditions.

It can be appreciated that as the detasseler enters or leaves a field, the present invention includes automatic modes to bring the pullers or cutters to the proper height. Moreover, the detasseler may be configured for travel on roads. The present invention also may include automatic steering to follow the rows. The present invention also provides for settings that position the toolbar at an appropriate height and folds the wings inward.

The detasseling operation of the present invention achieves gathering of data at the time of the mechanical cutting and/or pulling. With the navigational system, the precise location of the detasseler is known. Moreover, the sensors allow for determining the height of the plants when cutting is conducted and when pulling is conducted. The height of the plant after cutting is also known. This information is stored in the processor as well as transmitted in real time to a control center. The information may be used for analysis for optimizing the detasseling operations. The information may also be used for conducting other operations such as fertilization, irrigation, application of pesticides and/or herbicides, harvest and other operations. The information may also be used for timing of such operations as well as predicting crop yield.

The gathering and analysis of information from many detasseling operations provides for optimizing operations across a wide area and for managing equipment and other resources.

A detasseler apparatus comprises:
 a chassis;
 a head, the head supporting a plurality of row units, each of the row units having an independently adjustable vertical position;
 each of the row units comprises:
  a cutter assembly;
  a height adjustment assembly for varying height of the cutter;
  an optical sensing assembly; the optical sensing assembly comprises:
   a first photoelectric sensor at a first sensor height;
   a second photoelectric sensor at a second sensor height, the first sensor height being above the second sensor height;
   a processor for receiving and storing detasseling data.

These features of novelty and various other advantages that characterize the invention are pointed out with particularity in the claims annexed hereto and forming a part hereof. However, for a better understanding of the invention, its advantages, and the objects obtained by its use, reference should be made to the drawings that form a further part hereof, and to the accompanying descriptive matter, in which there is illustrated and described a preferred embodiment of the invention.

BRIEF DESCRIPTION OF THE DRAWINGS

Referring now to the drawings, wherein like reference numerals and letters indicate corresponding structures throughout the several views:

FIG. 20 is a front view of a second informational display for the detasseling apparatus shown in FIG. 1;

FIG. 22 is a front view of a fourth informational display for the detasseling apparatus shown in FIG. 1;

DETAILED DESCRIPTION OF THE PREFERRED EMBODIMENT

Figure 1:
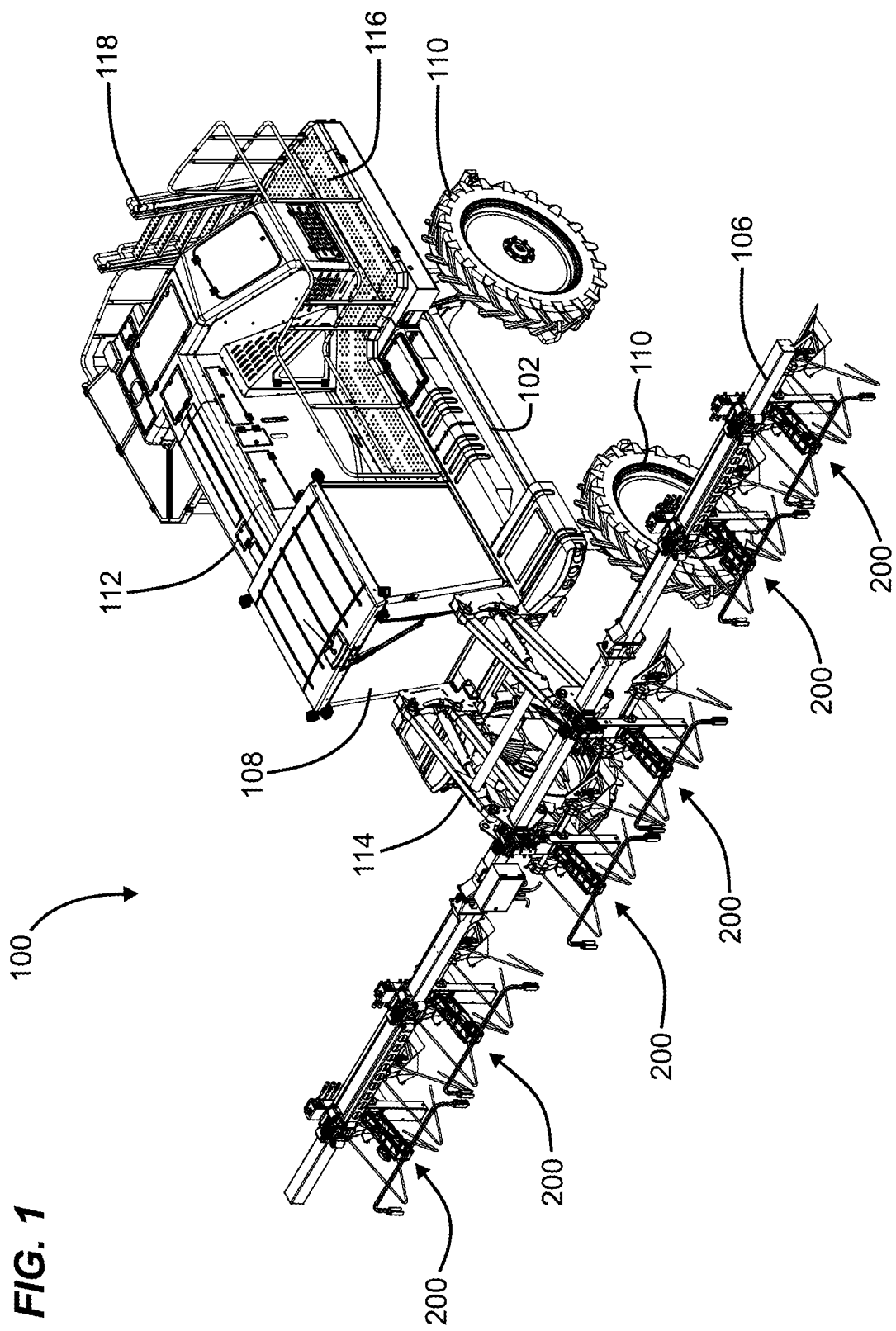
FIG. 1 is a front perspective view of a detasseling apparatus according to the principles of the present invention.
Figure 2:
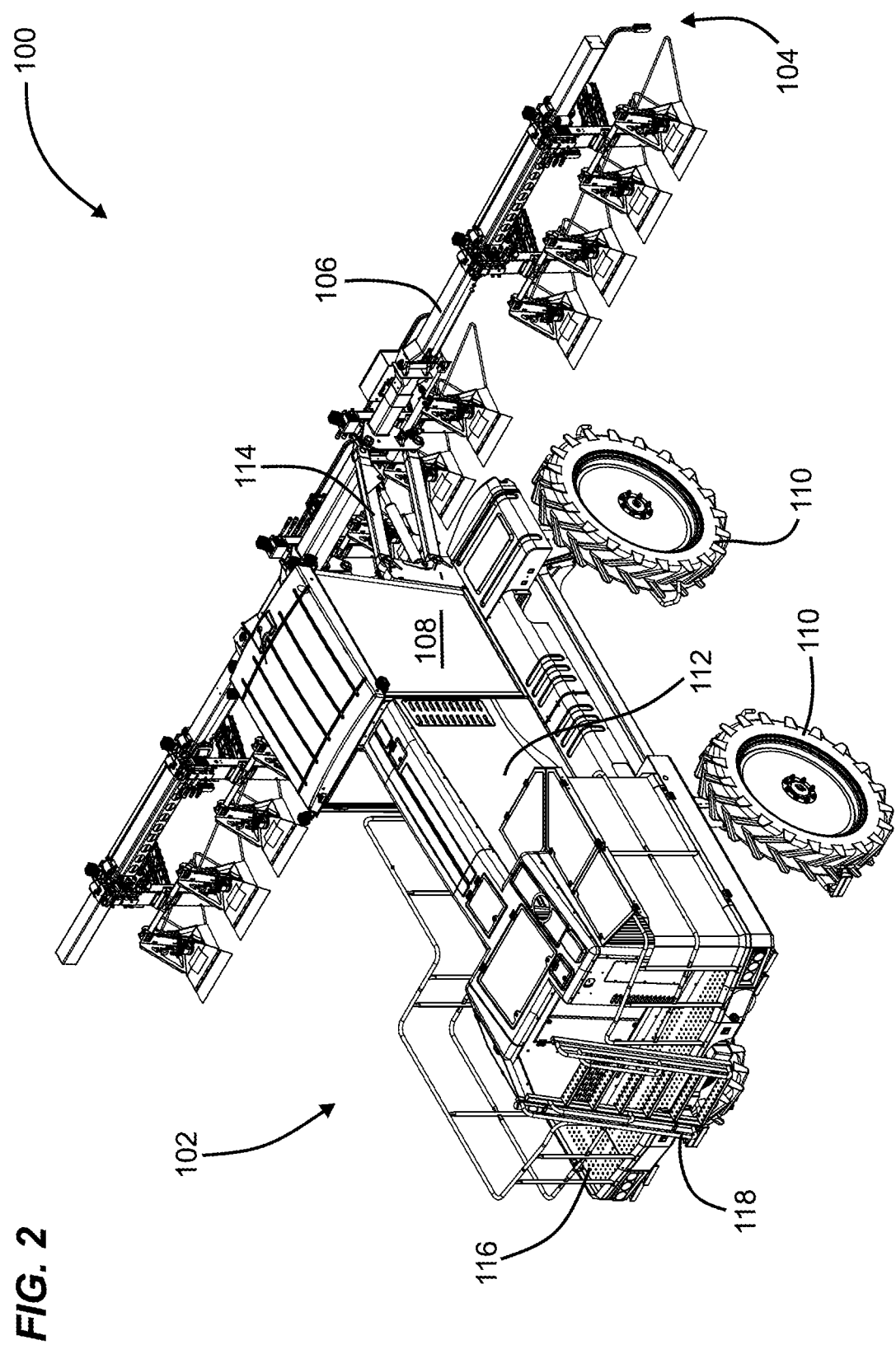
FIG. 2 is a rear perspective view of the detasseling apparatus shown in FIG. 1.
Figure 3:
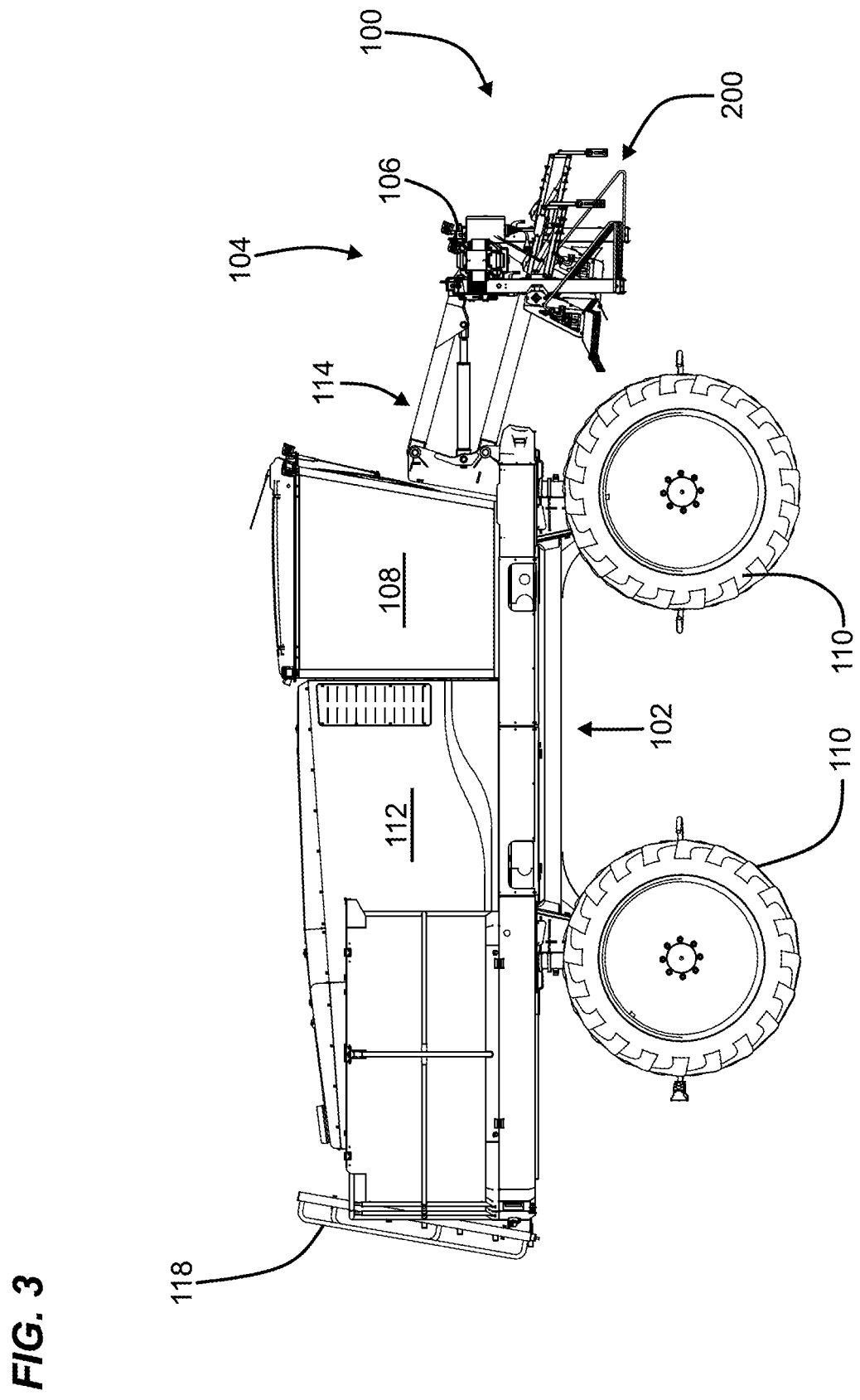
FIG. 3 is a side elevational view of the detasseling apparatus shown in FIG. 1.
Figure 4:
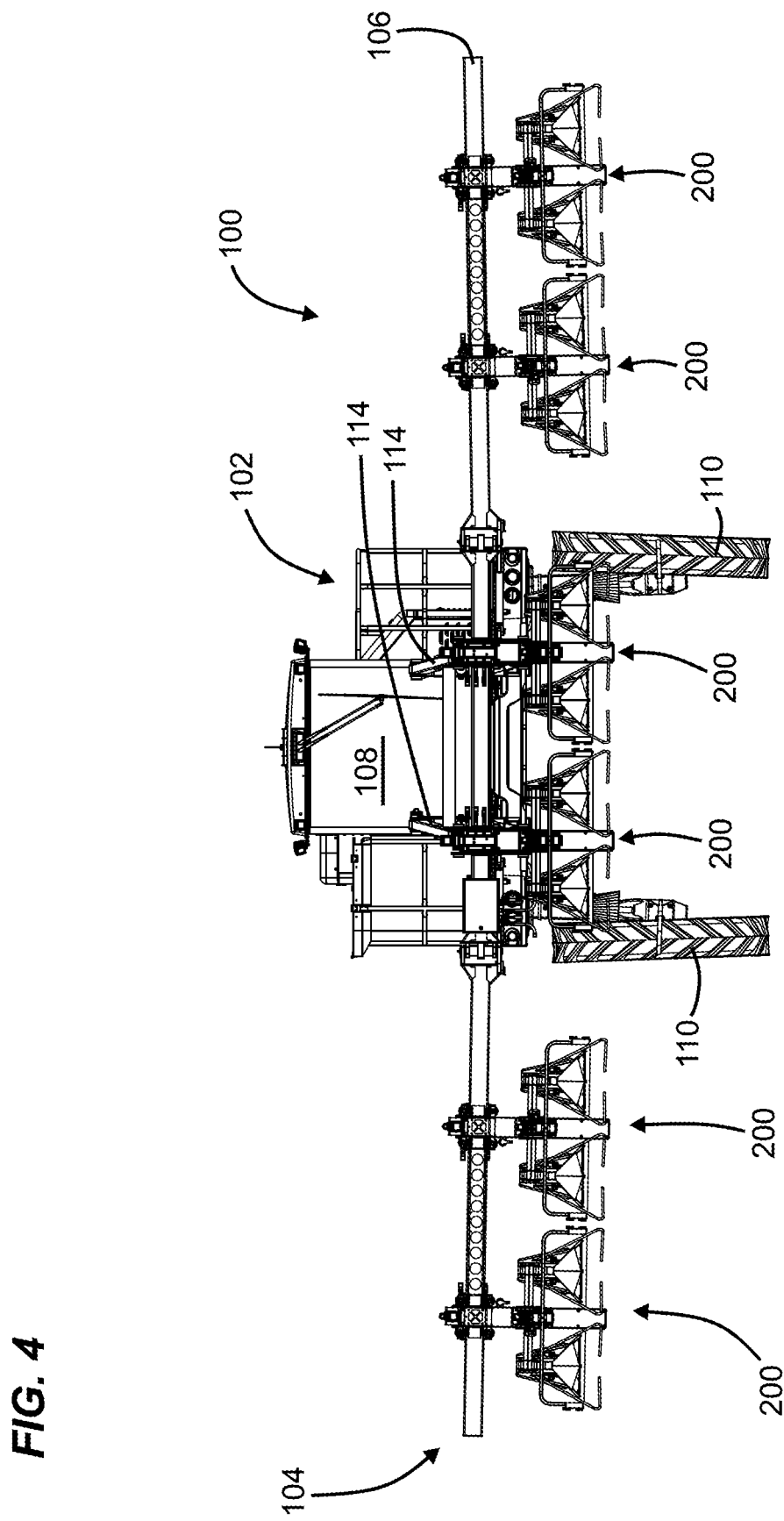
FIG. 4 is a front elevational view of the detasseling apparatus shown in FIG. 1.
Figure 5:
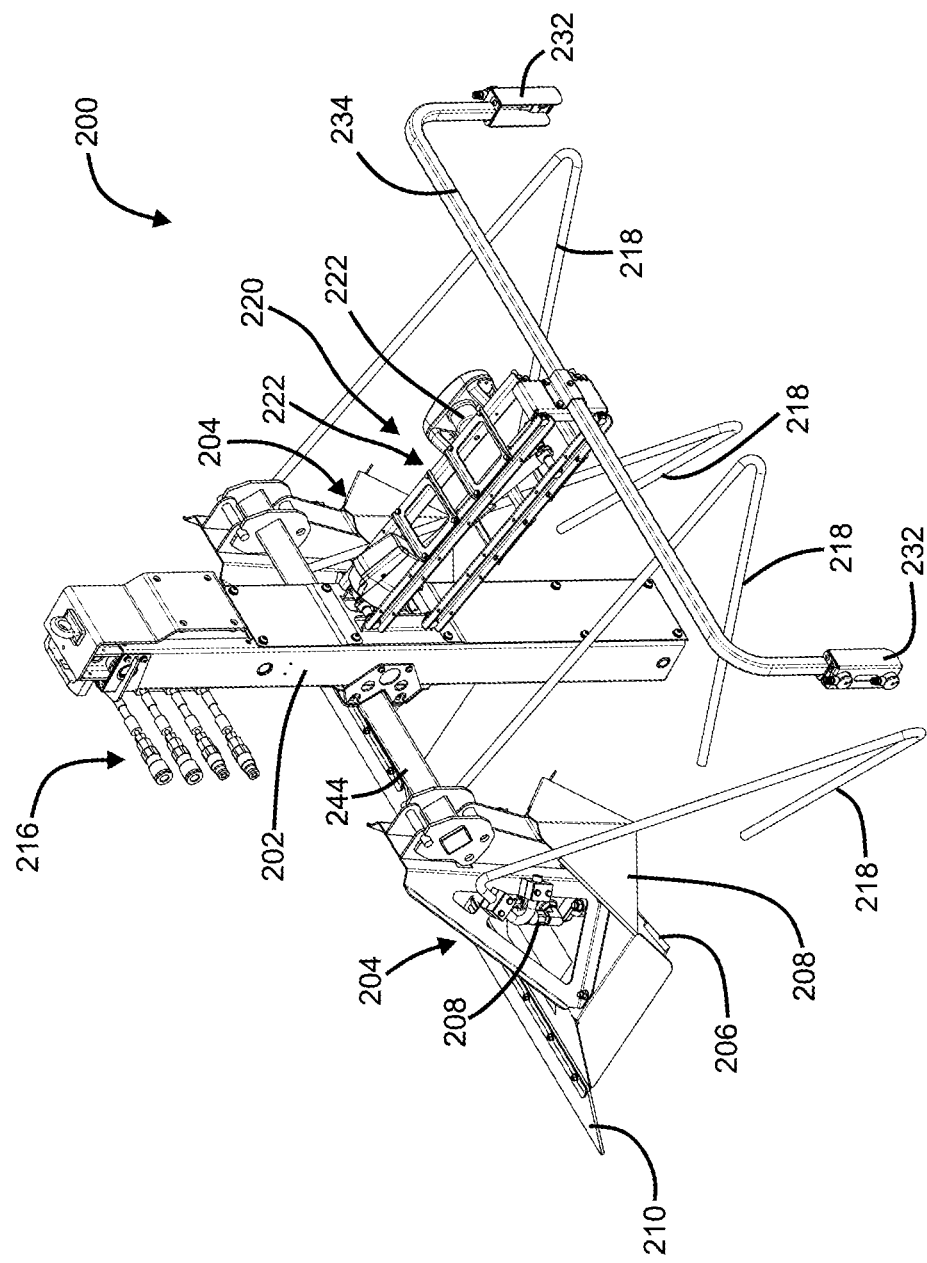
FIG. 5 is a perspective view of a row unit with a dual cutter assembly for the detasseling apparatus shown in FIG. 1.
Figure 6:
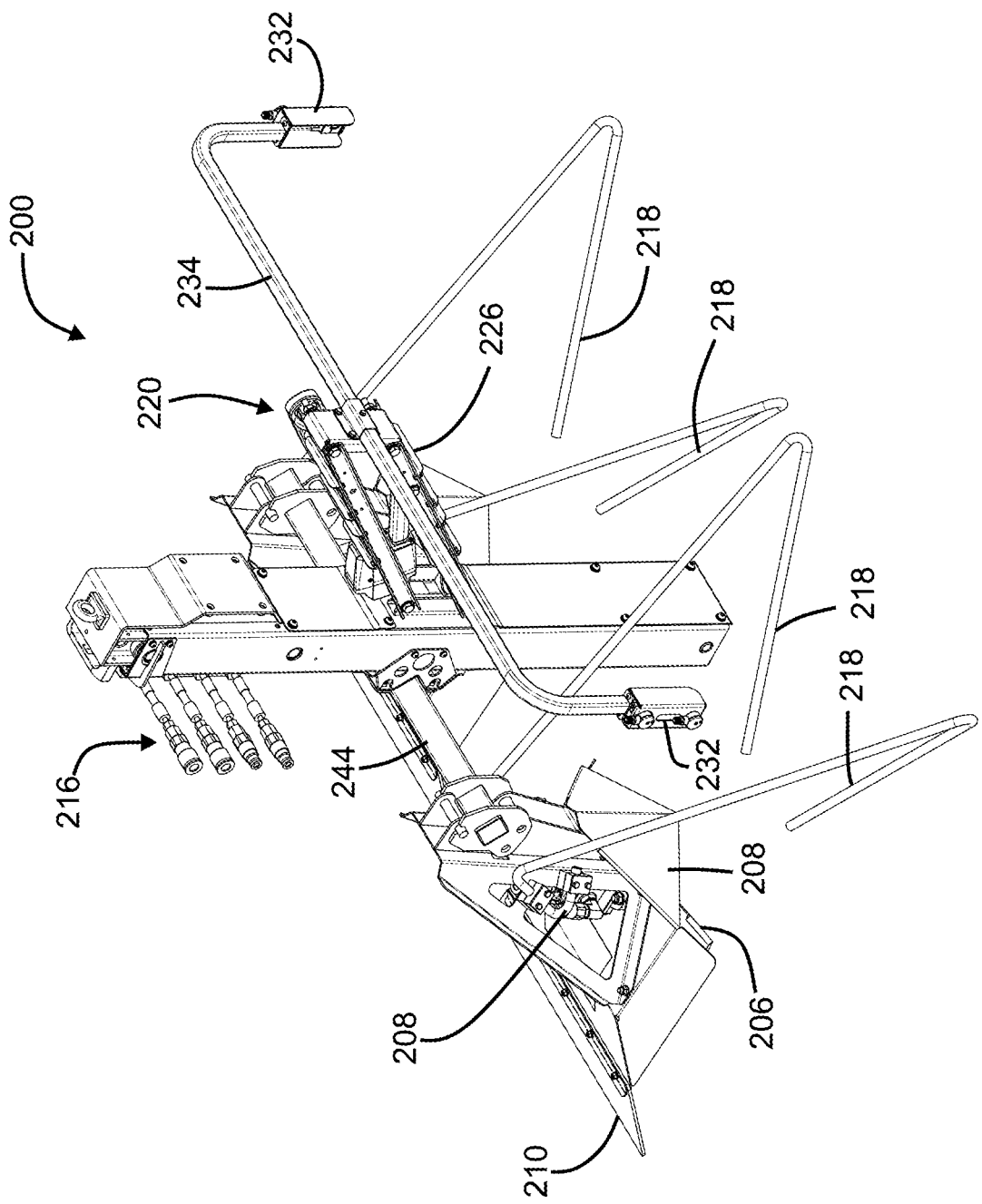
FIG. 6 is a perspective view of the row unit shown in FIG. 5 with the sensors in a raised position.
Figure 7:
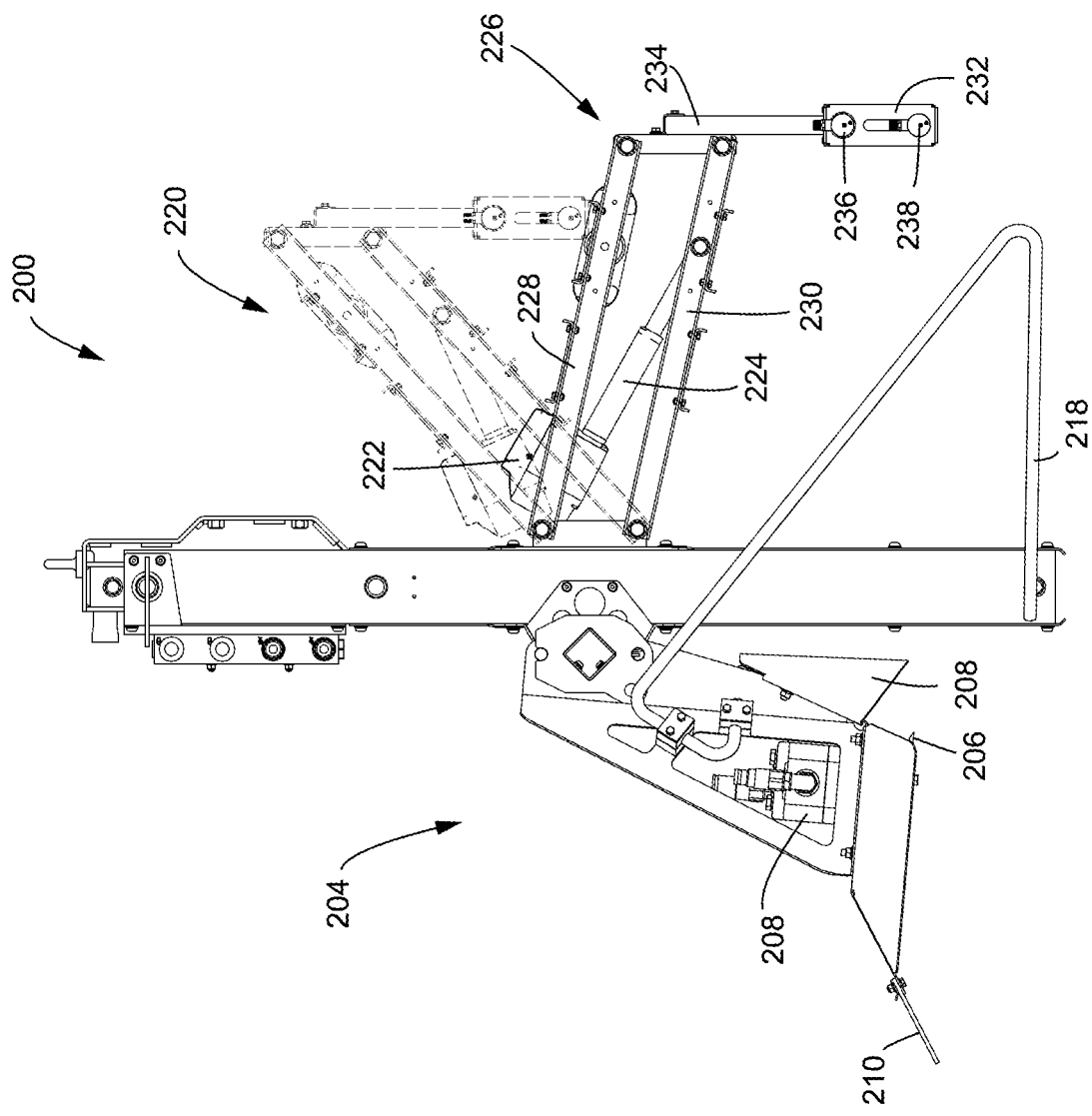
FIG. 7 is a side elevational view of the row unit shown in FIG. 5 with the raised sensor position of FIG. 6 shown in phantom.
Figure 8:
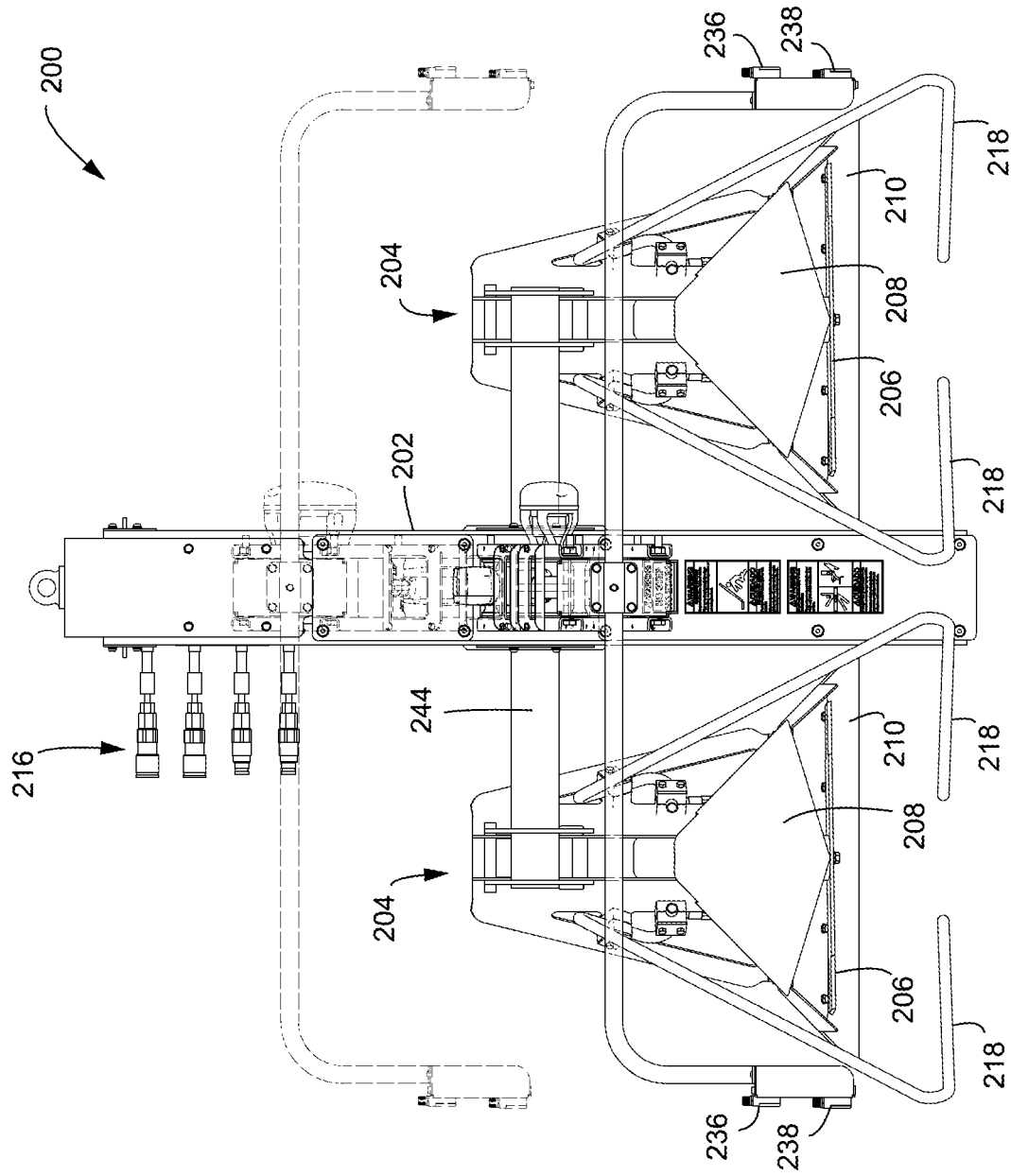
FIG. 8 is a front plan view of the row unit shown in FIG. 5 with the raised sensor position of FIG. 6 shown in phantom.

A detasseler system, generally designated (100), is shown in FIGS. 1-4. The detasseler includes a chassis (102) supporting a detasseling head (104). The head (104) includes a toolbar (106) supporting multiple row units (200). The toolbar (106) is mounted on a supporting linkage (114) to adjust the height of the toolbar (114) supporting the row units (200). The chassis (102) is typically supported on four wheels (110) and includes a cab (108) and a motor (112). It can be appreciated that the chassis (102) may be configured for use in applications other than detasseling such as supporting sprayers or other agricultural implements. The detasseling head (104) is therefore interchangeable with other types of heads performing other agricultural tasks. It can be appreciated that the wheels (110) maintain the chassis (102) high off the ground so that it may drive over tall plants such as corn and cause minimal damage to the field.

Figure 14:
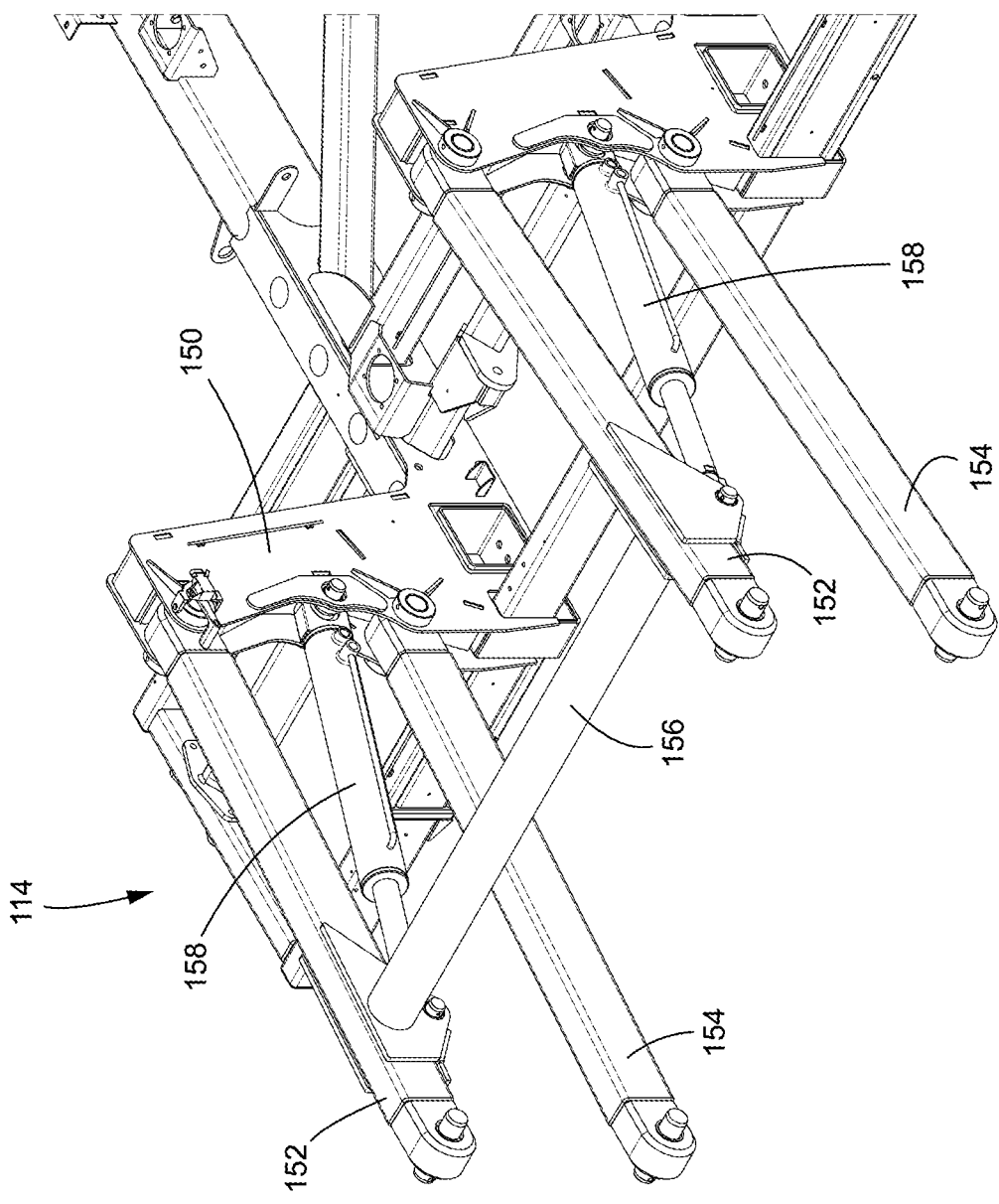
FIG. 14 is perspective view of a toolbar support linkage for the detasseling apparatus shown in FIG. 1.
Figure 15:
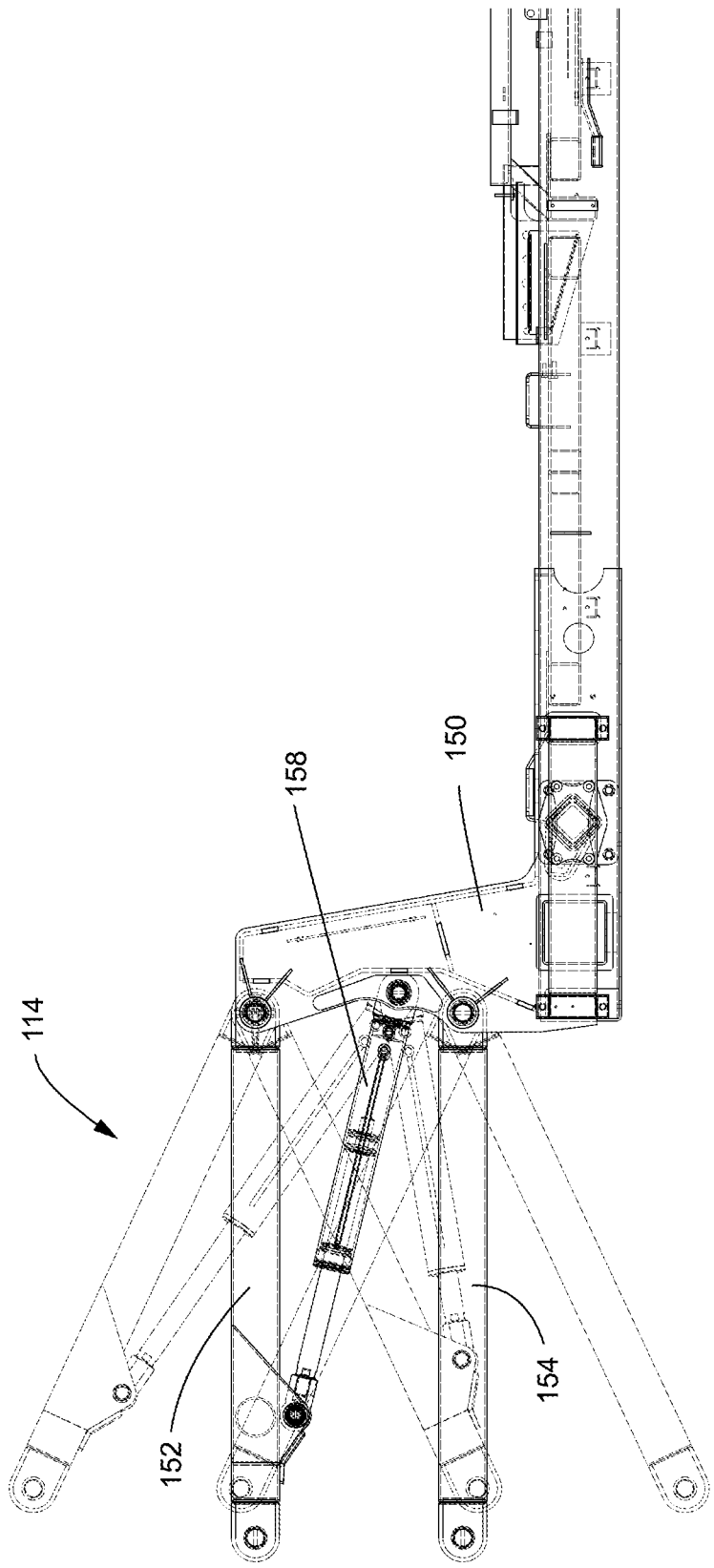
FIG. 15 is a side elevational view of the toolbar support linkage of FIG. 14 with multiple other positions shown in phantom.

The detasseling head (104) includes both the support linkage (114) and the toolbar (106). It can be appreciated that the toolbar (106) may have folding outer sections that fold rearward for travel and storage. The toolbar support linkage (114) shown in FIGS. 14 and 15 provides for adjusting the height of the entire toolbar (106) and includes sensors detecting the position of the head (104). As explained hereinafter, row units (200), which each include two cutters, or row units (300), which include two pullers, are individually adjustable for more precise and more efficient detasseling. A single linkage assembly (114) mounts the toolbar (106) to the chassis (102). The linkage (114) includes a frame assembly (150) attached to the chassis (102). A pair of upper links (152) and lower links (154) are pivotally mounted to the frame (150) as well as to the head (106). Hydraulic cylinders (158) extend and retract to raise and lower the linkage (114). Cross members (156) provide added support and stability. By extending and retracting the hydraulic cylinders (158), the upper links (152) and lower links (154) pivot upward and downward and therefore adjust the overall height of the toolbar (106) as shown in FIG. 15.

It can be appreciated that for some applications, mechanical cutting and pulling operations and performed. Cutting is first performed to remove a portion of the top leaves of the seed corn plant and improve access to increase the number of tassels successfully pulled. Care must be taken not to remove too much of the leaves as this may adversely affect seed production. In a few days after cutting, tassels have grown out and may be mechanically pulled from the plants. The combination of pulling and cutting ensures that a sufficiently high percentage of tassels of the female plants are removed to conduct cross-pollination. The pulling operation previously has generally been conducted manually. However, according to the present invention, cutting and pulling may both be performed mechanically with the detasseling system (100). With the control and responsiveness of the detasseling system (100) present invention, greater percentage of detasseling is achieved, thereby reducing or eliminating manual pulling operations while achieving a sufficiently pure hybrid seed.

In the embodiment shown, the toolbar (106) includes sections extending laterally to the left and the right and support a total of six row units (200). The row units (200) each include two cutters (204). In the embodiment shown in FIGS. 1-4, there are six row units (200), but fewer or more row units (200) may be used. The row units (200) are configured so that each row unit (200) includes two individual cutters (204) that are able to cut the tops of two rows of corn. There is a space between the center row units (200) and the outer row units (200) to accommodate the rows of "male" corn plants, which are not engaged and left with the tassels intact.

Referring now to FIGS. 5-10, a first embodiment of row units (200) is shown in greater detail. Each of the row units (200) is mounted on a framework (202). Each row unit (200) include two cutters (204) with each of the cutters (204) supported on a cross member (244). The height of the row units (200) is adjustable so that both cutters (204) move up and down together.

Figure 9:
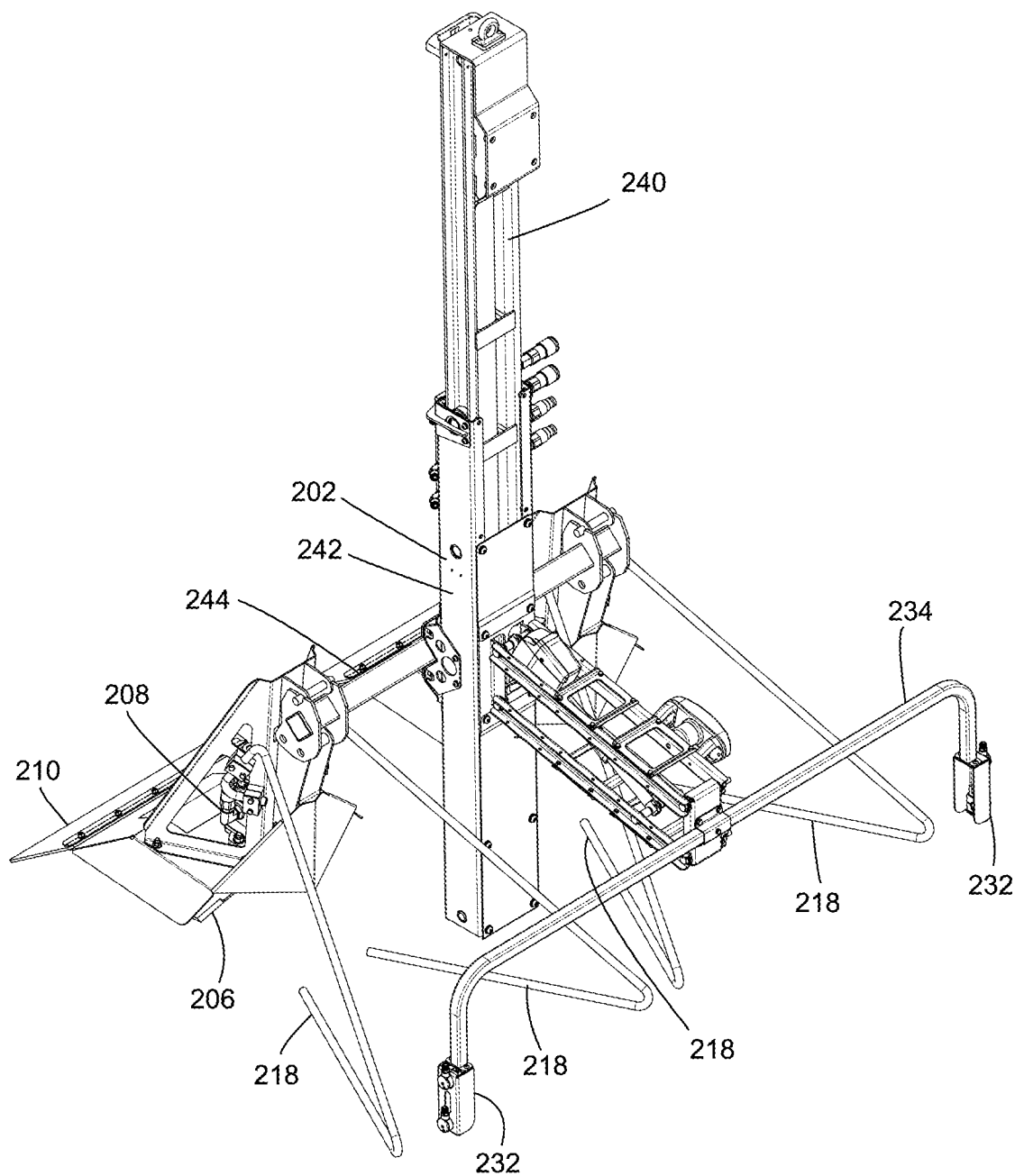
FIG. 9 is a perspective view of the row unit shown in FIG. 5 supported in a lowered position on the vertical cylinder.
Figure 10:
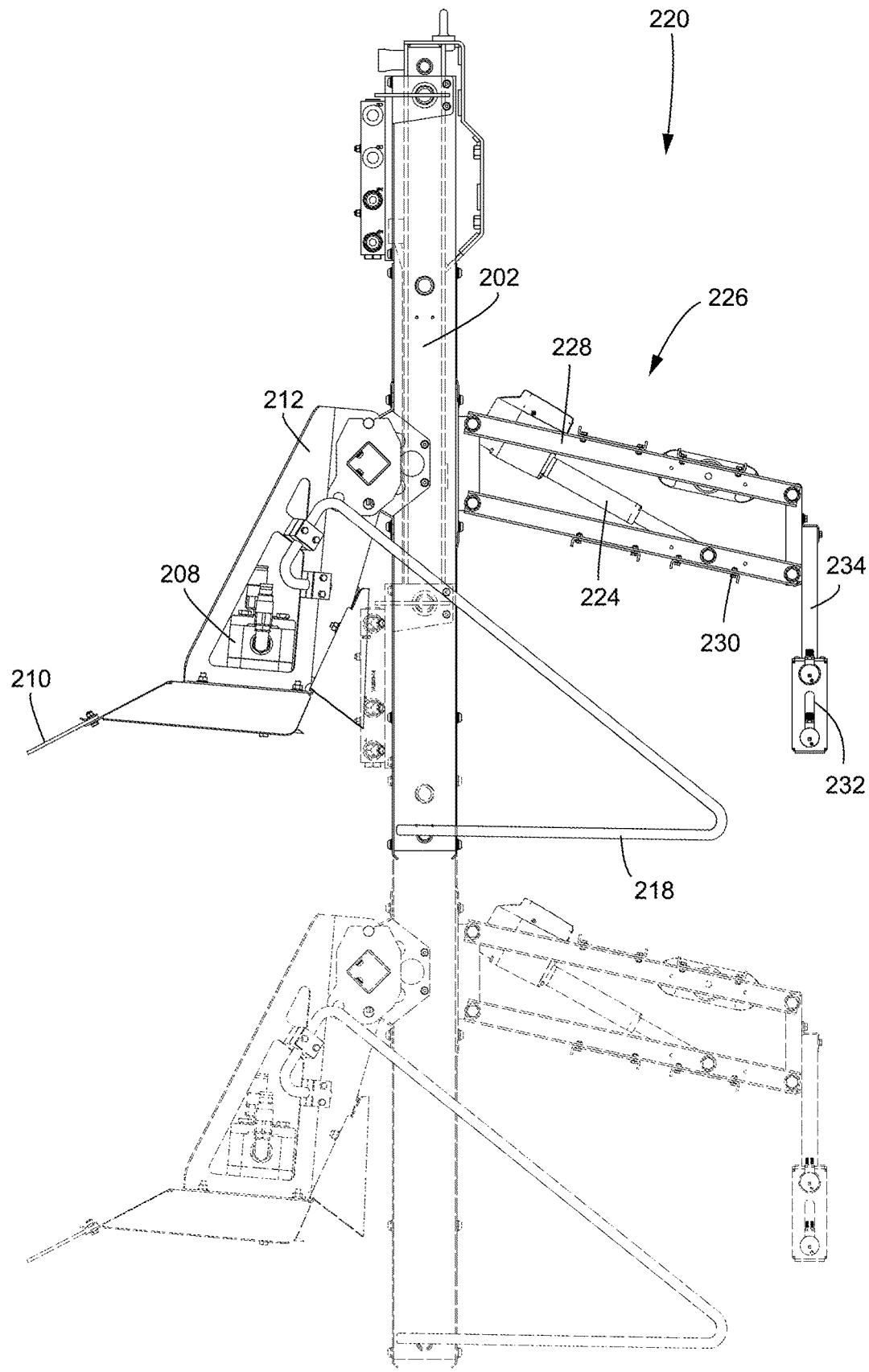
FIG. 10 is a side elevational view of the row unit shown in FIG. 5 supported in a raised position on the vertical cylinder and with the dual cutter assembly supported at a lowered position on the vertical cylinder shown in phantom.

The framework (202) supports and arranges hydraulic lines (216). The framework (202) also supports a cutter bracket (212) and a height adjustment assembly (220). The framework (202) is extendible as shown in FIG. 10 and may be moved from a position, such as shown in FIGS. 5-8, to a different height, such as shown in FIG. 9.

Each of the cutters (204) includes a support bracket (212). The support bracket (212) supports a hydraulic motor (208) that drives rotary cutting blades (206). The hydraulic motor (208) is connected to one of the hydraulic lines (216). The blades (206) rotate throughout a substantially horizontal plane to engage the tops of the corn plants and remove the optimal amount without imparting further damage to the corn plants. A shield (214) protects the motor (208) and prevents the plants from catching on the bracket (212). The bracket (212) forms somewhat of a peak to divert corn stalks to one side or the other to the path of the blades (206). A rear rubber flap (210) provides for a smooth disengagement from the cutter assemblies (204) after passing over the corn plants. The individual plants are directed toward the cutters (204) by guides (218) and extend forward beyond the framework (202) and include portions funneling the plants toward the center of the shield (214) and the blades (206).

A height adjustment assembly (220) mounts to the framework (202) and extends forward. The height adjustment assembly (220) includes linkage (226) having a linear actuator (224), an upper link (228) and a lower link (230), shown most clearly in FIGS. 7 and 10. The linkage (226) supports a sensor support bracket (238), which in turn supports opposed optical sensor assemblies (232). The linkage (224) is raised or lowered by extending or retracting the linear actuator (224), which pivots the other links (228, 230).

The optical sensor assemblies (232) are laterally opposed so that they pass on either side of two rows of corn that are engaged by the cutters (204). The opposed sensor assemblies (232) include an upper sender/receiver sensor pair (236) and a lower sender/receiver sensor pair (238) on each assembly. The opposed optical sensor assemblies (232) therefore can detect whether the optical path between the pair of upper optical sensors (236) is blocked or unblocked and whether the optical path between the opposed lower (238) is blocked or unblocked. The upper optical sensors (236) and the lower optical sensors (238) are therefore able to determine where the top of the corn plants between the pairs of sensors is. It can be appreciated that to maintain the tops of the corn plants at a height between the upper sensors (236) and lower sensors (238), the height adjustment assembly (220) is adjusted so that the optical path between the lower optical sensors (238) is blocked, but the optical path between the upper optical sensors (236) is open. To maintain proper cutting height, a row unit (200) is lowered if the optical path between the lower optical sensors (238) is not blocked. The height of the row units (200) is raised if the optical path between the opposed upper optical sensors (236) is blocked. It can be appreciated that the liner actuator (224) is extended and retracted to move the height adjustment assembly (220). Moreover, this position may be varied, as shown in the difference between FIGS. 5 and 6 and as shown in alternate positions in FIGS. 7, 8 and 10. The offset between the sensors and the cutters or between the sensors and the pullers is different, the row units (200, 300) may be set up for the proper offset for either cutting or pulling and for differences due to different varieties of seed corn.

To maintain proper cutting height, the row unit (200, 300) is lowered if the optical path between the lower optical sensors (238) is not blocked. The height of the row unit is raised if the optical path between the opposed upper optical sensors (236) is blocked. In a first operating condition, the beams of both the upper and lower pair of sensors (236, 238) are received. In such a condition, the row unit (200 or 300) is too high and will be lowered until the lower beam is not received. In a second operating condition, the beam is received in the upper pair of sensors (236), but the beam is not received in the lower pair of sensors (238). In this second condition, the row unit (200 or 300) is at the proper height. In a third condition, both the upper and lower beams are not received by the sensor pairs (236, 238), indicating the row unit (200 or 300) is too low and will be raised until the beam is received by the upper sensors (236). It can be appreciated that the liner actuator (224) is extended and retracted to move the row units (200, 300) to the proper height.

Referring now to FIG. 9, it can be appreciated that the framework (202), which mounts to the toolbar (106) allows for individual adjustment of the row units (200). The framework includes a telescopically slidable inner portion (240) and outer portion (242). It can be appreciated that the present invention provides for adjusting the overall height of the toolbar (106) by lowering or raising the toolbar linkage (114). The present invention provides for further individual adjustment of each of the row units (200) and the two associated cutters (204) with the individual height adjustment assemblies (220). It can therefore be appreciated that variations in the plants may be generally adjusted for by the operator in the cab (108) to raise or lower the toolbar (106) by actuating the linkage and more precise control and height adjustment is made through the sensor assemblies automatically maintaining the cutters (204) at the proper height.

Figure 11:
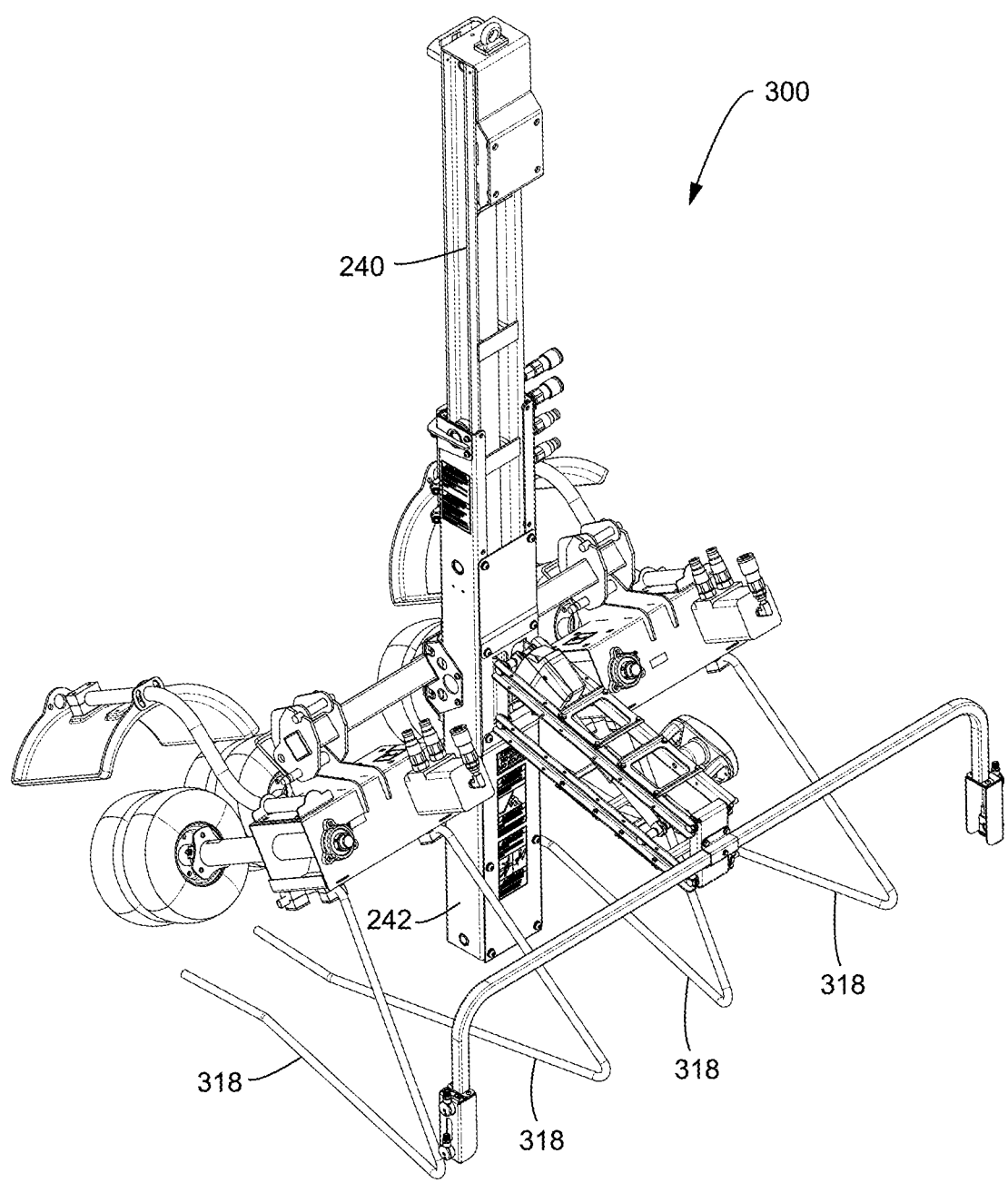
FIG. 11 is a perspective view of a second embodiment of a row unit with a dual puller assembly for use with the detasseling apparatus shown in FIG. 1.
Figure 12:
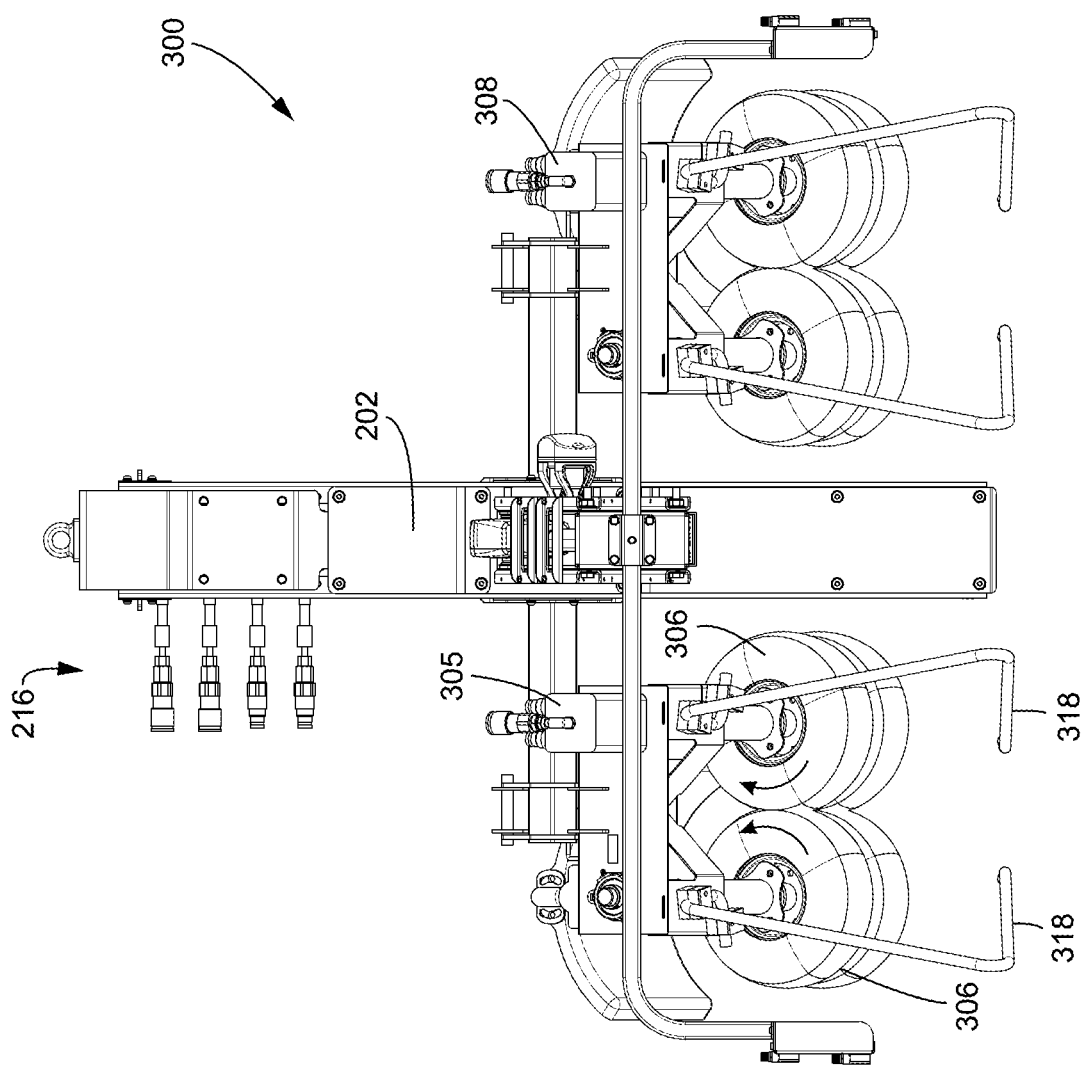
FIG. 12 is a front plan view of the row unit shown in FIG. 11.
Figure 13:
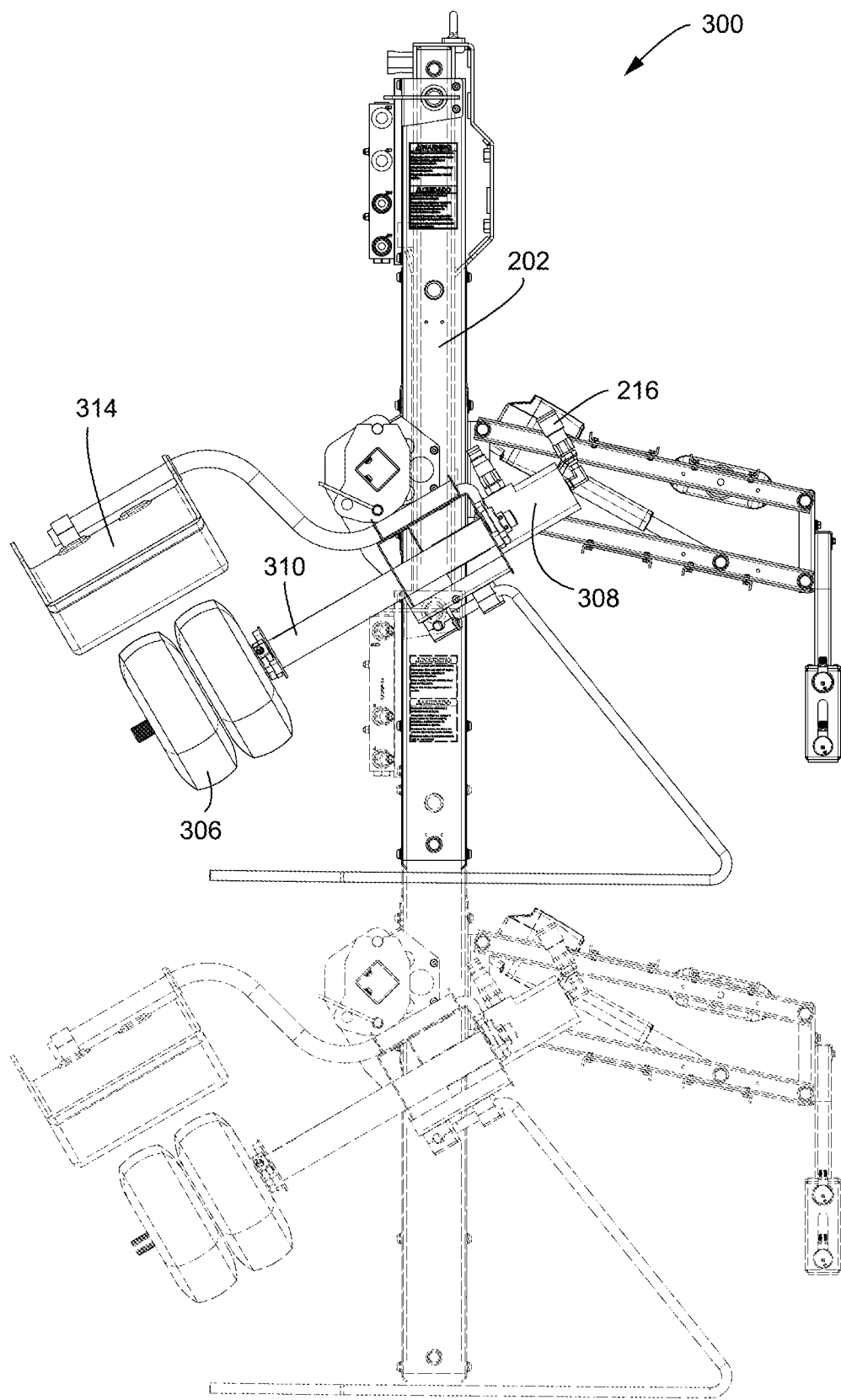
FIG. 13 is a side elevational view of the row unit shown in FIG. 11 and with a lowered position shown in phantom.

Referring now to FIGS. 11-13, there is shown a second embodiment of a row unit (300). The row unit (300) is a puller type detasseler that includes pullers (304) rather than cutters (204). The cutter and puller assemblies (204) and (304) may be interchangeably mounted and removed from the row unit cross member (244), as explained below. Quick connect/disconnect hydraulic connections through the hydraulic lines (216) simply need to be changed. The row units (300) detachably mount to the framework (202) and attach to the hydraulic lines (216) with quick disconnects. The row units (300) include guides (218) in a configuration similar to that for the cutter-type row units (200). The height adjustment assembly (220) is also maintained. For the puller row units (300), each assembly includes a support bracket (312) supporting a pair of counter rotating opposed wheels, also referred to as tires (306). At least one of the tires is driven by a hydraulic motor (308) and a rotating shaft (310). Slightly different guides (318) direct the tassels to the point of engagement between each pair of opposed tires (306). The pressure between the tires (306) may be adjusted to vary the pulling aggressiveness. A curved discharge chute (314) extends over the rear exit of the counter rotating tires (306). The curved discharge chute (314) is mounted at an angle and curves along an axis substantially parallel to the rotational axis of the tires (306). The discharge chute (314) therefore directs portions of tassels removed downward and rearward. In operation, the row units (300) advance along the rows of corn with the plants being directed between the guides (318) to the center of the opposed counter rotating tires (306). The tires (306) pinch the tassel and is pulled from the remainder of the corn plant. Height adjustment is again maintained with the height adjustment assembly (220) operating in the same manner as with the cutter type row units (200) described above. It can be appreciated that the mechanized pulling of tassels substantially reduces the labor previously required for manual detasseling. Moreover, it has been found that the percentage of tassels removed is sufficiently high to meet the standards for cross-pollination of fields of seed companies to achieve a hybrid seed having acceptable purity.

Figure 16:
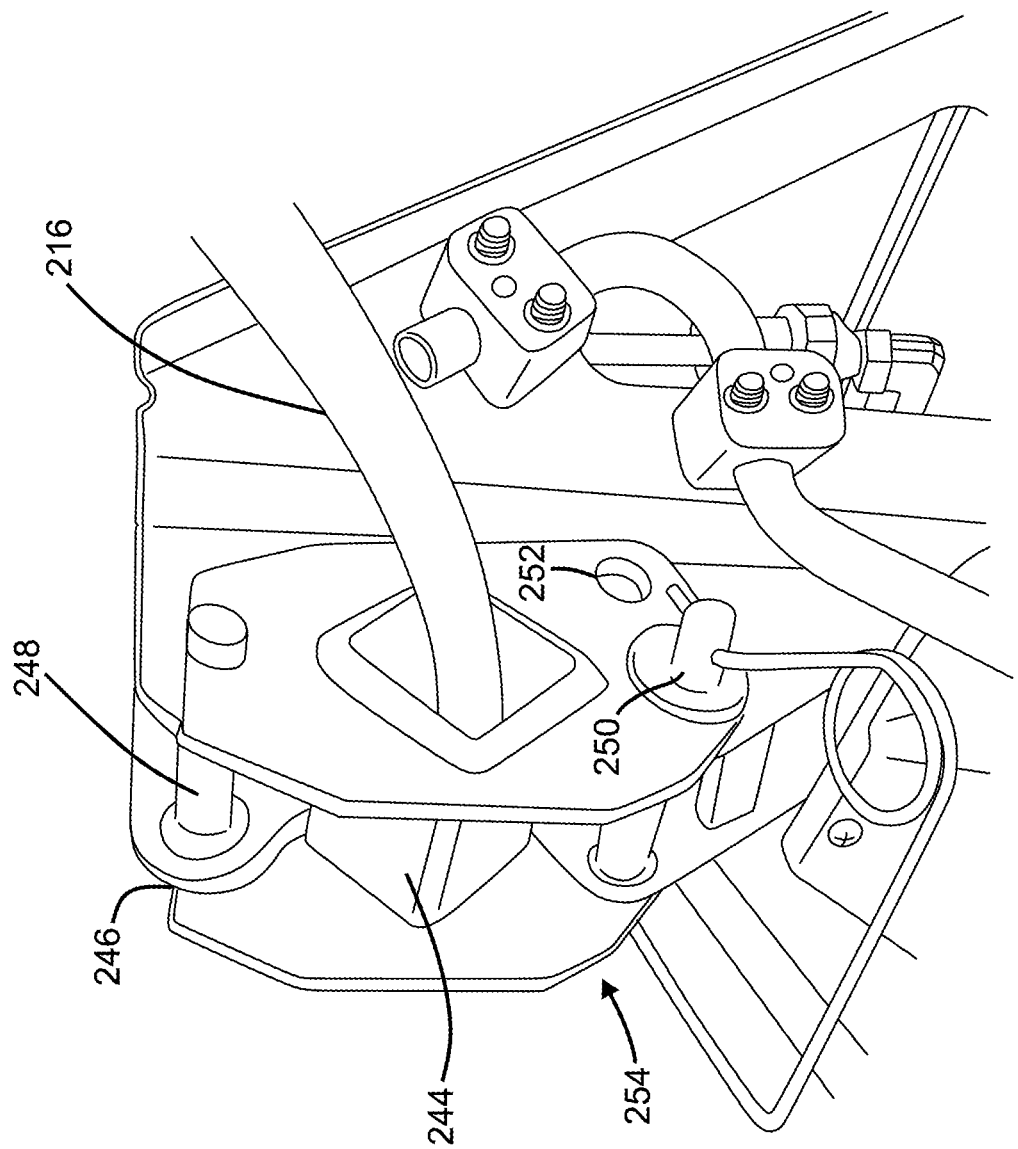
FIG. 16 is a perspective detail view of the mounting arrangement for a cutter assembly to a row unit.

FIG. 16 shows a mounting arrangement for a cutter type row unit (200). Each of the two cutters (204) for each row unit has a quick disconnect mounting. Moreover, the pullers (304) have similar mounting elements for interchangeably mounting and removal from the cross member (244). Hydraulic connections for the cutter or puller to the hydraulic lines (216) simply need to be changed. The cross member (244) includes a mounting cradle (246) that accepts a horizontally extending peg (248) of the cutter or puller assembly. A safety pin (250) extends through one of two lower receiving orifices (252) or (254). The position of the safety pin (250) mounting varies the angle of the cutter or puller (204, 304) for positioning either for use or for travel. It can be appreciated that the cutter or puller (204, 304) is quickly and easily mounted by lowering the peg (248) onto the cradle (246) and inserting the safety pin (250) to secure the cutter or puller assembly. To remove the cutter or puller assembly (204 or 304), the safety pin (250) is removed, the hydraulic line is disconnected and the cutter or puller (204 or 304) is simply lifted upward from the cradle (246). Only a single hydraulic line to the motor of the cutter or puller needs to be connected or disconnected and is routed through the cross member (244) to provide protection of the line and easy access to the connection.

Figure 23:
FIG. 23 is a side view of a corn plant.
Figure 24:
FIG. 24 is a side view of a corn plant with the tassel removed.

Referring to FIG. 23, it can be appreciated that prior to detasseling, a corn plant begins with the tassel fully attached and extending upward. However, after cutting and/or pulling, the "female" corn plants have no tassel, as shown in FIG. 24. It can also be appreciated that with standardized seed corn planting practices, the spacing of the present invention provides for passing over the male plants so their tassels are left intact, such as shown in FIG. 21, and therefore are able to cross-pollinate the female seed corn plants in the field.

The height of the corn at the time of cutting, the height of the corn after cutting, the depth of the cut and the height of the corn at the time of pulling can be determined and the data stored in the processor (1000), shown on displays (172) or transmitted to the control center (1020). Precise location information is provided by the navigation system (1006).

Figure 19:
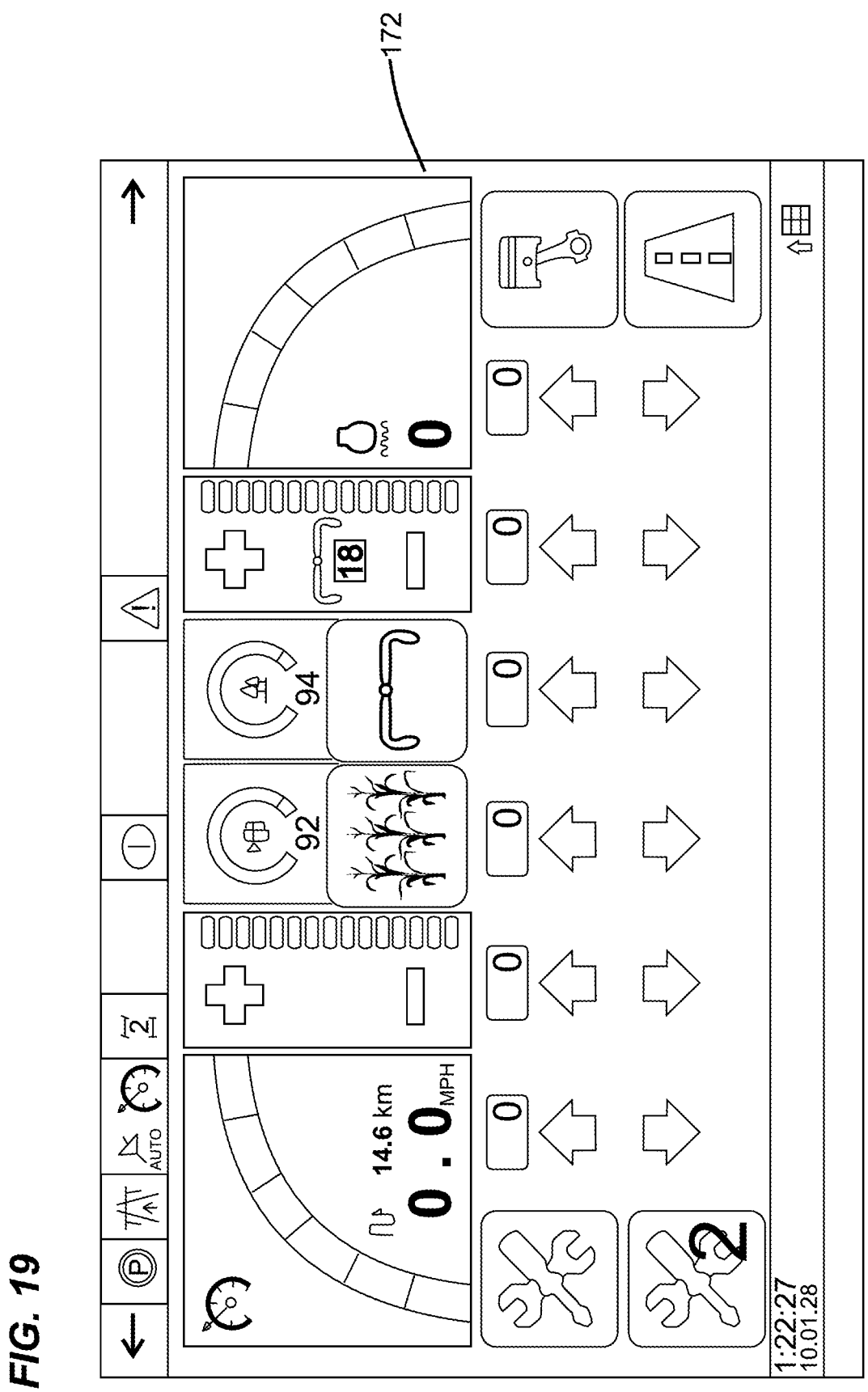
FIG. 19 is a front view of a first informational display for the detasseling apparatus shown in FIG. 1.
Figure 21:
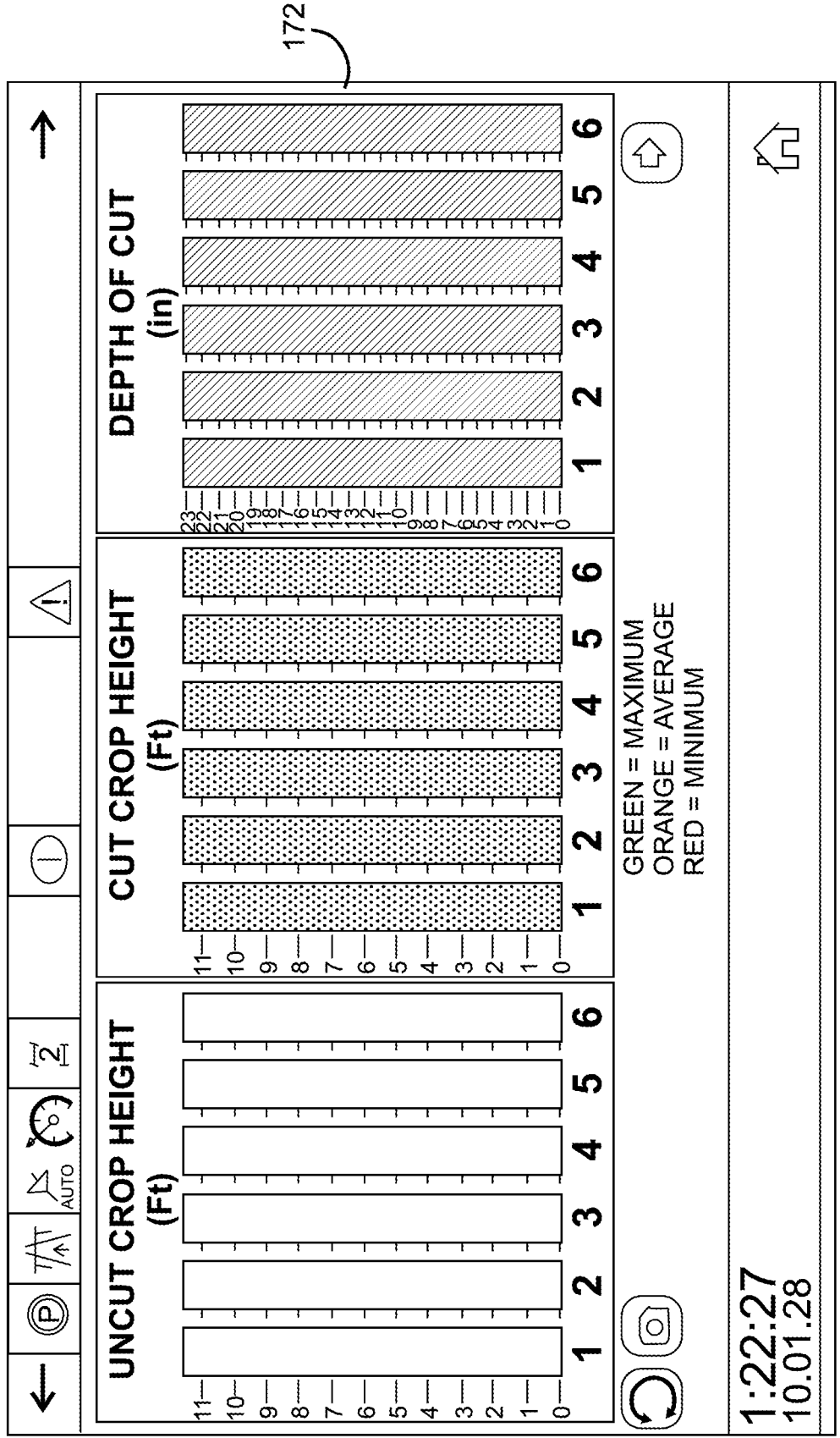
FIG. 21 is a front view of a third informational display for the detasseling apparatus shown in FIG. 1.

Referring now to FIGS. 19-22, the present invention also automatically acquires data on the corn in real time during the detasseling operations. Such information may be used for other operations and includes data such as the height of the corn. With use of GPS or other navigation systems (1006) on the detasseler (100), the precise location of the corn is pinpointed and its properties are measured to provide for mapping. In addition to acquiring various information, the present invention also includes a control system with a processor (1000) with interactive displays (172) in the cab for the operator to monitor the detasseling operations and to make adjustments as necessary. The various optical sensors (232), the position sensors 1002, 1004) on the adjustment linkages, suspension height sensors (1008) provide position information to determine the height of the various assemblies. The present invention may also include wireless technology and the processor (1000) may include a transmitter/receiver for providing real time information and downloading to a central database at control center (1020) at a remote location. The display screens (172) in the cab also provide an operator interface so that the operator may provide inputs (1010) to make adjustments as necessary. The display screen (172) in FIG. 19 provides for interactive adjusting of the offsets (174) and therefore the relative position of the optical sensors (232) to ensure that the optical sensors are at their proper vertical position relative to the pullers or cutters. The data acquired may also require raising or lowering the toolbar in unison. Various performance parameters of the detasseler (100) are also monitored and can be adjusted and optimized. As shown in FIG. 21, the height of the uncut plants, the height of the plants after cutting, and the depth of the cut can be determined and displayed, and may be compared for each of the row units as graphs. FIG. 22 shows summarized data relating minimum, maximum and average crop heights and cut depths for each row unit.

Figure 17:
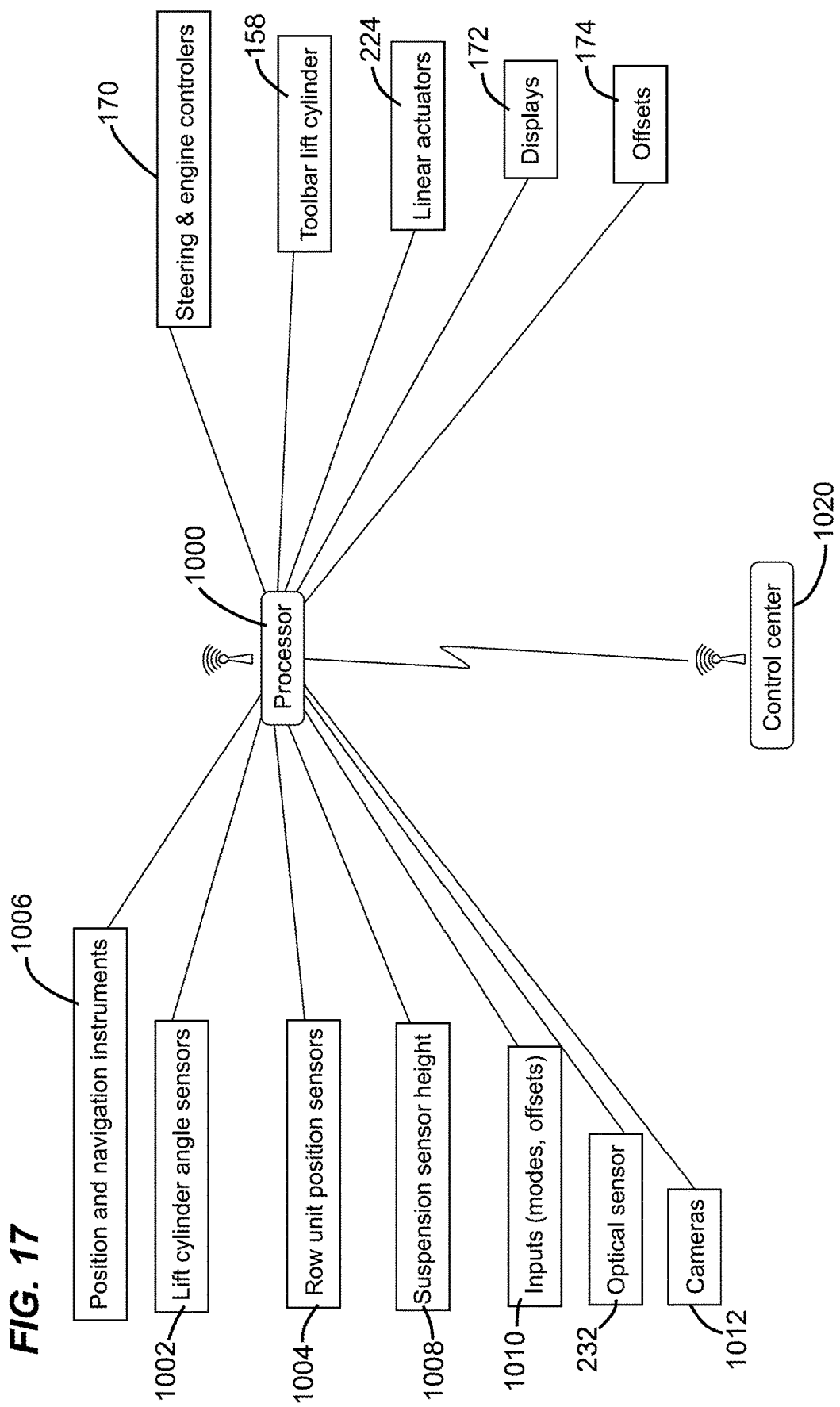
FIG. 17 is a diagrammatic view of the processor, inputs and remote fleet processor for the detasseler shown in FIG. 1.

As shown in FIG. 17, the present invention enables calibrating the sensors to ensure that the proper amount of the top of the plant is being cut relative to the beginning and end height information. It can also be displayed to show a comparison among each of the row units (200) or (300). Such display (172) provides for real time easily understood graphics that allow the operator to observe data including distance traveled, which allows the number of plants to be calculated, the relative uncut crop height, the cut crop height, depth of the cut, average, ranges and other relevant data. FIG. 20 also provides information related to minimum and maximum crop heights before and after cutting and the overall depth of the cut or pull for each of the six cutting or puller row units (200) or (300). The information provides for making adjustments prior to entering each field and to also making real-time on the fly adjustments as may be necessary, depending on the crop and operating conditions.

It can be appreciated that the optical sensor assemblies (232) sense the corn plants prior to the cutters (204) or pullers (304) engaging the plants as the detasseler (100) advances. It can be appreciated that the travel time to move upward and downward requires a short delay. The sensitivity of the row unit vertical travel changes the time needed to move up or down and the delay is also altered for maintaining accurate positioning. Therefore, the detasseler may include a programmed delay. The cutter (202) or puller (304) may otherwise be at a height for plants slightly ahead of their position. It can also be appreciated that as the detasseler (100) enters or leaves a field, an automatic mode provides for setting the cutters (204) or pullers (304) to the proper initial height and then makes a quick adjustment.

The detasseler (100) senses may aspects of the field, the individual plants and the operations performed. Referring now to FIG. 17, a processor (1000) collects data and information from multiple sensors, inputs and monitors. The processor controls the detasseler (100) and stores, analyzes, displays and/or transmits the information to a control center (1020) in real time. The processor controls many basic functions (170) of the detasseler (100). The processor includes automatic modes or manual operation. The processor provides for automatically positioning the toolbar for entry to a field and at the end of rows. The detasseler (100) includes cameras (1012) that allow for automatic steering to follow the rows in the field. The processor and controls (1000) also provide for configuring the detasseler (100) for travel on roads. The data on various aspects are collected in real time and can be utilized by the operator to make adjustments and corrections for improved performance. Moreover, the data is also transmitted to a control center (1020) at a remote location for further analysis and feedback. The position of the detasseler (100) is also known and allows for precise mapping. The detasseler (100) senses the top of the corn when cutting. The height of the chassis is known and by calculating the position of the linkages supporting the tool bar by inputs from sensors (1002) and the height of the row units relative to the chassis by inputs from sensors (1004), the height of the corn plants is determined. Moreover, as the offset between the optical sensors and the blades, the height of each of the cutters is known and therefore the height of the plant following cutting can be determined. Furthermore, the height of the corn plants can also be determined when pulling occurs. This information is stored in the processor (1000) on board the detasseler (100) and also transmitted to a remote location or locations (1020). The field manager and seed company may utilize this information to predict yields, project optimum dates for harvest, make adjustments for other detasseling and upcoming operations and determine whether follow up may be needed. The data may reveal patterns and or problems that may need addressing. As the information is collected in real time, it is also possible to provide feedback in real time make adjustments to the detasseler (100) during the detasseling operations to optimize the remaining operations.

The height of the corn at the time of cutting, the height of the corn after cutting, the depth of the cut and the height of the corn at the time of pulling can be determined and the data stored in the processor (1000), shown on displays (172) or transmitted to the control center (1020).

Precise location information is provided by the navigation system (1006). Using the know positions of the detasseler structures and geometry of the relative position of the various structures, the height of the corn can be determined. The height of the corn is determined by the position of the optical sensor assemblies (232). The optical sensor assemblies (232) are maintained at a position with the top of the corn between the upper optical sensor pair (236) and the lower optical sensor pair (238). The height of the corn is equal to the height of the optical sensor assemblies (232). The height of the optical sensor assemblies is determined using sensors to detect the height of the chassis and the mounting location of the support linkage (114) and the length and angle of the links (152, 154) supporting the toolbar (106) and the mounting location of the toolbar (106). The individual row unit heights can be determined by adding the height of the optical sensor assemblies (232) relative to the toolbar (106). The dimension of the links (228, 230) is known and the angle of the links (228, 230) and/or the extension of the linear actuator (224), which pivots the other links (228, 230) can be determined with sensors. The position of the optical sensors (232) relative to the cutting blades (206) or puller tires (306) is set by the operator. Therefore, the depth of the cut is set and known. Moreover, the height after cutting and the height of the puller tires (306) can be calculated by subtracting the depth of the cut from the height of the optical sensor assemblies (232).

Figure 18:
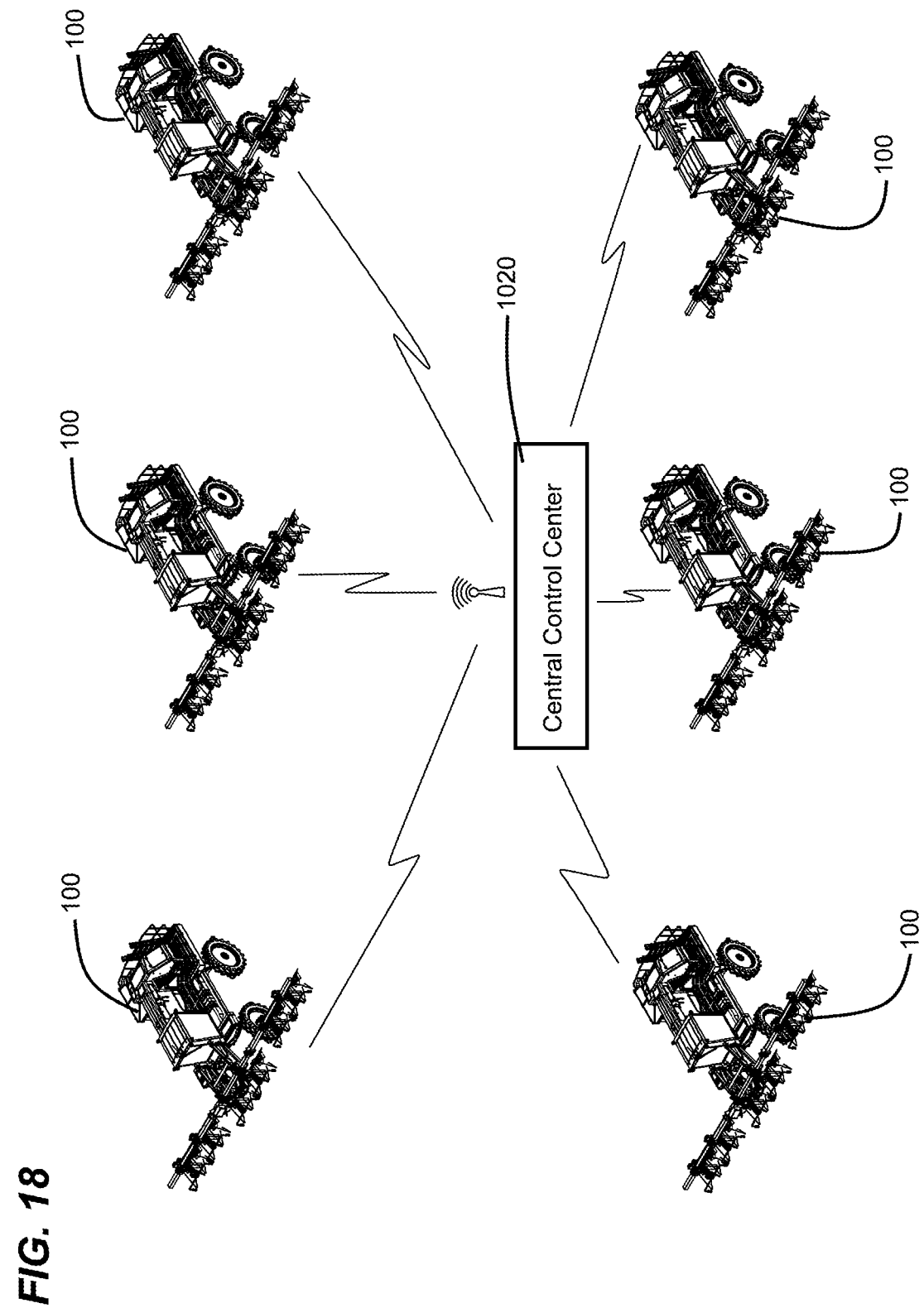
FIG. 18 is a diagrammatic view of a fleet of detasselers remote central fleet control.

As shown in FIG. 18, the present invention achieves collection from detasselers (100) at the time of multiple detasseling operations that may be utilized for further analysis and used for application of herbicides, pesticides, fertilizers and for irrigation and drainage. The information obtained may be analyzed together to provide direction with agricultural equipment. The information helps to plan when and where to perform future actions and provide yield predictions and to optimize crop yields.

The present invention therefore achieves a system and method that provides for complete mechanized automatic detasseling. Such a system provides for cutting a proper amount of the tops of corn plants or for maintains a proper height for engaging and pulling the tassels from the corn plants. Such an operation also provides greater information in real time than what has been possible with prior systems regarding the plants, the detasseling operation and the results of detasseling.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A corn detasseling apparatus, comprising:
 a chassis;
 a head, the head having a toolbar mounted on a toolbar supporting linkage to adjust a height of the toolbar, the toolbar supporting a plurality of row units, each of the row units comprising:
  a framework supporting a cross-member;
  two pullers or cutters supported on the cross-member;
  a height adjustment assembly comprising a telescoping assembly mounted on the framework cross-member for independently adjusting vertical position of the row unit to maintain the pullers or cutters at a predetermined height relative to corn plants being engaged;
  an optical sensing assembly associated with the row unit for sensing a top of corn plants; the optical sensing assembly comprising:
   an upper first photoelectric sensor sensing presence of a corn plant at a height of the first photoelectric sensor;
   a lower second photoelectric sensor sensing presence of a corn plant at a height of the second photoelectric sensor, the height of the first photoelectric sensor being above the height of the second photoelectric sensor;
   a processor for receiving and storing detasseling data from the first photoelectric sensor and from the second photoelectric sensor and controlling the height adjustment assembly.

2. The corn detasseling apparatus according to claim 1, wherein each of the row units comprises an opposed aligned sender and receiver pair of the first photoelectric sensors and an opposed aligned sender and receiver pair of the second photoelectric sensors.

3. The corn detasseling apparatus according to claim 1, wherein the opposed aligned pair of the first photoelectric sensors and the opposed aligned pair of the second photoelectric sensors include a sender spaced laterally outward from a first side of the row unit and a receiver spaced laterally outward from a second side of the row unit.

4. The corn detasseling apparatus according to claim 1, further comprising guides spaced forward of the pullers or cutters along a direction of travel for guiding corn plants to the pullers or cutters.

5. The corn detasseling apparatus according to claim 1, wherein the pullers and the cutters are interchangeably mountable.

6. The corn detasseling apparatus according to claim 5, wherein the puller comprises a pair of opposed rotating wheels configured for severing a corn plant as the corn plant passes between the rotating wheels.

7. The corn detasseling apparatus according to claim 1, wherein the head includes a first height adjustment for raising and lowering the head.

8. The corn detasseling apparatus according to claim 7, wherein each of the row units comprises a second height adjustment for raising and lowering each of the row units.

9. The corn detasseling apparatus according to claim 1, further comprising a support assembly and a plurality of sensors for controlling position of the head and the row unit and acquiring data on the position of the head and row unit, comprising:
 a linkage changing elevation of the head and a position sensor determining height of the head;
 a row unit linear actuator and a row unit position sensor determining a height of the row unit relative to the head.

10. The corn detasseling apparatus according to claim 1, further comprising a cab and operator interactive controls and displays.

11. The corn detasseling apparatus according to claim 1, wherein the processor comprises storage, display and/or transmission of the following information for each cutting assembly for data selected from the group consisting of:
 crop height prior to cutting;
 overall crop height after cutting;
 cut depth;
 crop height during pulling;
 location.

12. A corn detasseling apparatus, comprising:
 a chassis;

a head supporting a plurality of row units, each of the row units comprising:
a framework;
a cross member removably mounted on the framework; the cross member supporting one of:
a pair of interchangeable cutter assemblies, and
a pair of interchangeable puller assemblies;
each of the interchangeable cutter assemblies comprising:
a cutter assembly bracket,
one or more rotating blades,
a motor driving the one or more rotating blades,
a pair of first guides extending forward from the cutter assembly bracket along a direction of travel for guiding corn plants to the blades;
each of the interchangeable puller assemblies comprising:
a puller assembly bracket,
a pair of opposed counter rotating wheels,
a motor driving at least one of the wheels,
a pair of second guides extending forward from the puller assembly bracket along a direction of travel for guiding corn plants to the opposed wheels;
a height adjustment assembly for independently adjusting vertical position of the row unit to maintain the puller assemblies or cutter assemblies at a predetermined height relative to corn plants being engaged;
an optical sensing assembly associated with the row unit for sensing a top of corn plants; the optical sensing assembly comprising:
an upper first photoelectric sensor sensing presence of a corn plant at a height of the first photoelectric sensor;
a lower second photoelectric sensor sensing presence of a corn plant at a height of the second photoelectric sensor, the height of the first photoelectric sensor being above the height of the second photoelectric sensor;
a processor for receiving and storing detasseling data from the first photoelectric sensor and from the second photoelectric sensor and controlling the height adjustment assembly.

13. The corn detasseling apparatus according to claim 12, wherein each of the brackets comprise a shield forward of the bracket along the direction of travel.

14. The corn detasseling apparatus according to claim 12, wherein each of the cutter assemblies comprises a flexible flap extending rearward from the cutter assembly bracket along the direction of travel.

15. The corn detasseling apparatus according to claim 12, wherein each of the puller assemblies comprises a discharge chute extending rearward from the puller assembly bracket along the direction of travel.

16. The corn detasseling apparatus according to claim 15, wherein the wheels rotate about a rotational axis extending obliquely relative to the ground and the discharge chute extends obliquely relative to the ground and curves along an axis substantially parallel to the rotational axis of the wheels.

17. A corn detasseling apparatus, comprising:
a chassis;
a head supporting a plurality of row units, each of the row units comprising:
a framework;
a cross member removably mounted on the framework; the cross member supporting one of:
a pair of interchangeable cutter assemblies, and
a pair of interchangeable puller assemblies;
a height adjustment assembly for independently adjusting vertical position of the row unit to maintain the puller assemblies or cutter assemblies at a predetermined height relative to corn plants being engaged;
an optical sensing assembly associated with each of the row units for sensing a top of corn plants; wherein the height adjustment assembly comprises a parallel motion linkage mounting the optical sensing assembly.

18. The corn detasseling apparatus according to claim 17, wherein the parallel motion linkage comprises a vertical actuator.

19. The corn detasseling apparatus according to claim 17, wherein the parallel motion linkage extends diagonally forward and upward and supports optical sensors at a forward end of the parallel motion linkage to move the optical sensors along an arcing path.

20. The corn detasseling apparatus according to claim 19, wherein the parallel motion linkage imparts parallelogram motion between the optical sensor and the vertical movement of the following cutter assemblies or puller assemblies.

21. The corn detasseling apparatus according to claim 17, wherein the parallel motion linkage comprises a first link comprising the framework; a second link comprising an upper link; a third link comprising a sensor support bracket; and a fourth link comprising a lower link.

22. The corn detasseling apparatus according to claim 17, wherein the parallel motion linkage comprises the framework; an upper link pivotally connected to the framework at a first end and pivotally connected to a sensor support bracket at a second end, and a lower link parallel to the upper link, the lower link being pivotally connected to the framework at a first end and pivotally connected to the sensor support bracket at a second end.

23. The corn detasseling apparatus according to claim 17, each of the interchangeable cutter assemblies comprising:
a cutter assembly bracket,
one or more rotating blades,
a motor driving the one or more rotating blades,
a pair of first guides extending forward from the cutter assembly bracket along a direction of travel for guiding corn plants to the blades;
each of the interchangeable puller assemblies comprising:
a puller assembly bracket,
a pair of opposed counter rotating wheels,
a motor driving at least one of the wheels,
a pair of second guides extending forward from the puller assembly bracket along a direction of travel for guiding corn plants to the opposed wheels.

24. The corn detasseling apparatus according to claim 17, wherein the optical sensing assembly comprises:
an upper first photoelectric sensor sensing presence of a corn plant at a height of the first photoelectric sensor;
a lower second photoelectric sensor sensing presence of a corn plant at a height of the second photoelectric sensor, the height of the first photoelectric sensor being above the height of the second photoelectric sensor;
a processor for receiving and storing detasseling data from the first photoelectric sensor and from the second photoelectric sensor and controlling the height adjustment assembly.

* * * * *